(12) United States Patent
Accola et al.

(10) Patent No.: US 7,312,033 B2
(45) Date of Patent: Dec. 25, 2007

(54) CFTR ALLELE DETECTION ASSAYS

(75) Inventors: Molly Accola, Madison, WI (US); Susan S. Wigdal, Madison, WI (US); Andrea L. Mast, Oregon, WI (US); Christian T. Bartholomay, Madison, WI (US); Robert W. Kwiatkowski, Jr., Verona, WI (US); Vincent Tevere, Madison, WI (US); Hon S. Ip, Madison, WI (US)

(73) Assignee: Third Wave Technologies, Inc., Madison, WI (US)

( * ) Notice: Subject to any disclaimer, the term of this patent is extended or adjusted under 35 U.S.C. 154(b) by 199 days.

(21) Appl. No.: 10/371,913

(22) Filed: Feb. 21, 2003

(65) Prior Publication Data

US 2004/0096844 A1 May 20, 2004

Related U.S. Application Data

(60) Provisional application No. 60/426,144, filed on Nov. 14, 2002.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 5,614,402 A | | 3/1997 | Dahlberg et al. |
| 5,795,763 A | | 8/1998 | Dahlberg et al. |
| 5,834,181 A | * | 11/1998 | Shuber .......................... 435/5 |
| 5,843,669 A | | 12/1998 | Kaiser et al. |
| 5,846,717 A | | 12/1998 | Brow et al. |
| 5,985,557 A | | 11/1999 | Prudent et al. |
| 5,994,069 A | | 11/1999 | Hall et al. |
| 6,001,567 A | * | 12/1999 | Brow et al. .................... 435/6 |
| 6,090,543 A | | 7/2000 | Prudent et al. |
| 6,090,606 A | | 7/2000 | Kaiser et al. |
| 6,183,960 B1 | | 2/2001 | Lizardi |
| 6,194,149 B1 | | 2/2001 | Neri et al. |
| 6,210,884 B1 | | 4/2001 | Lizardi |
| 6,235,502 B1 | | 5/2001 | Weissman et al. |

| | | | |
|---|---|---|---|
| 2003/0152942 A1 | * | 8/2003 | Fors et al. ............... 435/6 |

FOREIGN PATENT DOCUMENTS

| WO | WO 97/27214 | 7/1997 |
|---|---|---|
| WO | WO 98/23774 | 6/1998 |
| WO | WO 98/42873 | 10/1998 |
| WO | WO9850403 | 11/1998 |
| WO | WO 01/90337 A2 | 11/2001 |
| WO | WO0198537 | 12/2001 |
| WO | WO 02/070755 A2 | 9/2002 |

OTHER PUBLICATIONS

Boehringer Mannheim (1997 Biochemicals Catalog, p. 95).*
Sigma-Aldrich Techware Laboratory Equipment and Supplies (1995-1996, p. 213).*
Fors et al. (Pharmacogenomics, vol. 1, No. 2, pp. 219-229, 2000).*
Zielenski et al. (Genbank Accession No. M55115, Jan. 2001).*
Heim, et al., Genetics in Medicine 3(3):168-176 (2001).
Raman, et al., Pediatrics 109(1): E13 (2002).
Dumur, et al., Hum Genet 97: 7-10 (1996.
Grody, Cutting, et al., Genetics in Medicine 3(2):149-154 (2001).
Grody and Desnick, Genetics in Medicine 3(2):87-90 (2001).
Rosenstein and Cutting, Journal of Pediatrics 132(4): 589-595 (1998).
LeGrys, Laboratory Medicine 33(1): 55-57 (2002).
Wilson, et al., Journal of Pediatrics 132 (4): 596-599 (1998).
Gregg, et al., Pediatrics 99(6): 819-824 (1997).
Rock, et al., Pediatrics 85(6): 1001-1007 (1990).
Kerem, et al., Science 245: 1073-1080 (1989).
Riordan, et al., Science 245: 1066-1073 (1989).
Rommens, et al., Science 245: 1059-1065 (1989).
Bobadilla, et al., Human Mutation 19: 575-606 (2002).
Noone and Knowles, Respiratory Research 2(6):328-332 (2001).
Rohlfs, et al., Genetics in Medicine 4(5):319-323 (2002)).
Kiesewetter, et al., Nature Genetics 5(3): 274-278 (1993).
Fujimura, Northup et al. N Engl J Med., Jan. 4; 322(1):61 (1990).
Lyamichev et al., Nat. Biotech., 17:292 (1999).
Hall et al., PNAS, USA, 97:8272 (2000).
Reynaldo et al., J. Mol. Biol. 97: 511-520 (2000).

* cited by examiner

*Primary Examiner*—Jeanine A. Goldberg
(74) *Attorney, Agent, or Firm*—Casimir Jones, S.C.

(57) ABSTRACT

The present invention provides compositions and methods for the detection and characterization of mutations associated with cystic fibrosis. More particularly, the present invention provides compositions, methods and kits for using invasive cleavage structure assays (e.g. the INVADER assay) to screen nucleic acid samples, e.g., from patients, for the presence of any one of a collection of mutations in the CFTR gene associated with cystic fibrosis. The present invention also provides compositions, methods and kits for screening sets of CFTR alleles in a single reaction container.

2 Claims, 4 Drawing Sheets

Fig. 2

| Mutation | Exemplary Pool | 3' blocking group | Oligo type (Arm) | Sequence (5'-3') | $\varepsilon_{260}$ M⁻¹cm⁻¹ |
|---|---|---|---|---|---|
| 2789+5G>A | 1 | none | invader | TTTGGTTGTGTGTGGCTCCTTGGAAAGTGAT (SEQ ID NO:1) | 330800 |
| 2789+5G>A | 1 | hex | probe/DM | CGCGCCGAGGAGTATATTCCATGTCCTATTGTG (SEQ ID NO:2) | 306500 |
| 2789+5G>A | 1 | none | synthetic target | CAATCTACACAATAGGACATGGAATATTCACTTTCCAAGGAGCCAGCACAACCAAA (SEQ ID NO:3) | 667000 |
| R1162X | 1 | none | invader | GTTTACCTTCTGTTGGCATGTCAATGAACTTAAAGACTCT (SEQ ID NO:4) | 428000 |
| R1162X | 1 | hex | probe/DM | CGCGCCGAGGAGCTCACAGATCGC (SEQ ID NO:5) | 253000 |
| R1162X | 1 | none | synthetic target | TCAGATGCGATCGTGTGAGCGAGTCTTTAAGTTCATTGACATGCCAAACAGAGGTAAAC (SEQ ID NO:6) | 659000 |
| R347P | 4 | none | invader | CAGGAAATTGCCGAGTGACCGCCATGT (SEQ ID NO:7) | 306600 |
| R347P | 4 | hex | probe/ER24 | ACGGACGCGGAGCAGAACAATGCAG (SEQ ID NO:8) | 318200 |
| R347P | 4 | none | synthetic target | CTCATTCTGCATTGTTCTGCCCATGGCGGTCACTCGGCAATTTCCCTGGG (SEQ ID NO:9) | 488000 |
| 1898+1G>A | 4 | none | invader | GACTCTCCTTTTGGATACCCTAGATGTTCTTGAACAGAAAAGAAATATTTGAAAGT (SEQ ID NO:10) | 619900 |
| 1898+1G>A | 4 | hex | probe/DM | CGCGCCGAGGATATGTTCTTGAATACCTTACTTAT (SEQ ID NO:11) | 366500 |
| 1898+1G>A | 1 | none | synthetic target | ATAAGTAAGGTATTCAAAGAACATATCTTCAAATATTCTTTTCTGTTAAAACATCTAGGTATCCAAAGGAGAGTC (SEQ ID NO:12) | 904800 |
| 2184delA | 4 or 5 | none | invader | CCCCAAACTCTCCAGTCTGTTTAAAAGATTATTTTTC (SEQ ID NO:13) | 393000 |
| 2184delA | 4 or 5 | hex | probe/DM | CGCGCCGAGGGTTTCTGTCCAGGAGACA (SEQ ID NO:14) | 305200 |
| 2184delA | 4 or 5 | none | synthetic target | GCTTTGATGACGCTTCTATCTATCATCATAGGAAACACCAAT (SEQ ID NO:15) | 509300 |
| delI507 | 1 | none | invader | CGCGCCGAGGATATTCTTTCTTTAATGGTGCC (SEQ ID NO:16) | 345200 |
| delI507 | 1 | hex | probe/DM | GCCTGGCACCATTAAAGAAAATATCTTTGGTGTTTCCTATGATGAATATAGATACAGAAGCGTCATCAAAGCATGCC (SEQ ID NO:18) | 866600 |
| delI507 | 1 | none | synthetic target | GCCCTTCGGCGATGTTTTTCTGGAGATTTATGTTCTATGT (SEQ ID NO:19) | 409100 |
| G85E | 4 | none | invader | ACGGACGCGGAGAAAATCTTTTTATATTTAGGGGTAAG (SEQ ID NO:20) | 431700 |
| G85E | 4 | hex | probe/ER24 | AGATCCTTACCCCTAAATATAAAAAGATTTCATAGAACATAAATCTCCAGAAAAAACATCGCCGAAGGGCATTA (SEQ ID NO:21) | 869300 |
| G85E | 4 | none | synthetic target | AATCATAGCTTCCTATGACCCGGATAACAAGGAGAACT (SEQ ID NO:22) | 443800 |
| R117H | 3 | none | invader | CGCGCCGAGGACTCTATCGCGATTTATCT (SEQ ID NO:23) | 304200 |
| R117H | 3 | hex | probe/DM | ATGCCTAGATAAATCGGCATAGAGTTCTTCCTCCTTGTTATCCGGGTCATAGGAAGCTATGATT (SEQ ID NO:24) | 681700 |
| R117H | 3 | none | synthetic target | CATGAATGCAGTTTACACAGAACAATGCTTCGTAGACAATAAGTAGTTATTCACT (SEQ ID NO:25) | 595000 |
| R560T | 1 | none | invader | ACGGACGCGGAGGTTGCTAAAGAAATTCTTGCT (SEQ ID NO:26) | 378100 |
| R560T | 1 | hex | probe/ER24 | CAACGAGCAAGAATTTCTTTAGCAACGTGAATAACTAATTATTGGTCTCAGCAAGCATTTGCTGTGTAAATGTCATTCATGTAAAA (SEQ ID NO:27) | 945400 |
| R560T | 1 | none | synthetic target | GCAATTTGGATGACCTTCTGCCTCTTCACCATATTTGACTTCATCCAGT (SEQ ID NO:28) | 496000 |
| 3120+1G>A | 2 | none | invader | CGCGCCGAGGATATGTAAAAATAAGTACCGTTAA (SEQ ID NO:29) | 397500 |
| 3120+1G>A | 2 | hex | probe/DM | AGACATACTTAACGGTACTTATTTTACATATATGGATGAAGTCAAATATGGTAAGAGCAGAGAAGGTCATCCAAAATTGCTATATC (SEQ ID NO:30) | 884000 |
| 3120+1G>A | 2 | none | synthetic target | GAGAGTTGGCCATTCTTGTATGGTTTGGTTGACTTT (SEQ ID NO:31) | 372300 |
| 3659delC | 2 | none | invader | CGCGCCGAGGGTAGGTTACCTTCTGTGTTGG (SEQ ID NO:32) | 302800 |
| 3659delC | 2 | hex | probe/DM | CATGCCAACAGAAGGTAAACCTACAAGTCAACCAACCATACAAGAATGGCCAACTCTC (SEQ ID NO:33) | 679800 |
| 3659delC | 2 | none | synthetic target | CCTGAAAGATATAATTAAGATAGAAAAGAGGACACTTGTTGGT (SEQ ID NO:34) | 531000 |
| A455E | 1 | none | invader | ACGACGCGGAGGAGGTTGCTGGATCCA (SEQ ID NO:35) | 298100 |
| A455E | 1 | hex | probe/ER24 | CCAGTGCGGATCCAGCAACCTCCACAACTGTCCTTCTATCTTGAAATTAATATCTTTCAGG (SEQ ID NO:36) | 661000 |
| A455E | 2 | none | synthetic target | AGTGCATAGGGAAGCACAGATAAAAACACCACAT (SEQ ID NO:37) | 413500 |
| 1078delT | 2 | hex | probe/DM | CGCGCCGAGGGCTCTTCTTGCAGGGTTCTGTGGTGTTTTATCGTGCTTCCCTATGCACT (SEQ ID NO:38) | 355400 |
| 1078delT | 1 | none | synthetic target | AGCCTCTTCTTGCAGGGTTCTGTGGTGTTTTATCTGTGCTTCCCTATGCACT (SEQ ID NO:39) | 533300 |
| G551D | 2 | none | invader | GGAGAGAAGAACAGATAAATTCGGAAAGGTGGAATCCACTCACAGTGGAGT (SEQ ID NO:40) | 628200 |
| G551D | 2 | hex | probe/DM | CGCGCCGAGGATCAACGAGCAAGAAGAATTTCT (SEQ ID NO:41) | 343800 |
| G551D | 2 | none | synthetic target | CTTGCTAAAGAAATTCTTGCTCGTTGATCTCCACTCAGTGTGATTCCACCTTCTCCAAGAACTATATTGTCTTTCTCTGCAAACTT (SEQ ID NO:42) | 883100 |
| I148T | 1 | hex | probe/DM | AAATCAAACTAAACATAGCTATTCTTCTCATCTGCATTCCAT (SEQ ID NO:43) | 432400 |
| I148T | 1 | none | synthetic target | ACGGACGCGGAGGTGTGATGAAGGCCAAA (SEQ ID NO:44) | 350200 |
| I148T | 1 | hex | probe/ER24 | CCATATTCTTGATCACTCACCTAGCACTGGAATGGCAGATGCAAATGAGCAAGATGA (SEQ ID NO:45) | 643100 |
| N1303K | 2 | none | invader | CCGCGCCGAGGCTTCATCACTAATGTCCAGAAAAA (SEQ ID NO:46) | 414700 |
| N1303K | 2 | hex | probe/DM | CGCGCCGAGGCTTTTCTAAATGTTCCAGAAAAA (SEQ ID NO:47) | 391200 |
| N1303K | 2 | none | synthetic target | ATTTATTTTTCTGGAACATTTAGAAAAAAGTTGGATCCCTATGAACAGTGGAGTGATCAAGAAAATATGGAAAG (SEQ ID NO:48) | 867100 |
| 711+1G>T | 2 | none | invader | GCCTTTCCAGTTGTATTAATTTATAACATAAGTGCCTAAAGATTAAATCAATAGGTACATT (SEQ ID NO:49) | |
| 711+1G>T | 2 | hex | probe/ER24 | ACGGACGCGGAGAATTCATCAAATTTGTTCAGG (SEQ ID NO:50) | |
| 711+1G>T | 2 | hex | probe/DM | CGCGCCGAGGAATTCATCAAATTTGTTCAGGT (SEQ ID NO:51) | |

Fig. 2 (cont'd)

| Mutation | Exemplary Pool | 3' blocking group | Oligo type (Arm) | Sequence (5'-3') | ε₂₆₀ M⁻¹ cm⁻¹ |
|---|---|---|---|---|---|
| 711+1G>T | 2 | none | synthetic target | ACCTGAAACAAATTTGATGAATTATGTACCTATTGATTAATCTTTAGGCACTATTGTTATAAATTATACAACTGGAAAGGC (SEQ ID NO:52) | 927000 |
| 1717-1G>A | 3 | none | invader | GCCTTTCAAATTCAGATTGAGCATACTAAAAGTGACTCTCTAAATTTCTATTTTGGTAATAT (SEQ ID NO:53) | 685000 |
| 1717-1G>A | 3 | hex | probe/DM | CGCGCCGAGGAGACATCTCCAAGTTTGC (SEQ ID NO:54) | 294500 |
| 1717-1G>A | 3 | none | synthetic target | CTCTGCAAACTTGGAGATGTCTTATTACCAAAAATAGAAAATTAGAGAGTCACTTTTAGTATGCTCAATCTGAATTTGAAAGGCACATC (SEQ ID NO:55) | 1010000 |
| W1282X | 3 | none | invader | GCTCACCTGTGTATCACTCGGCAAAGTTTCCTA (SEQ ID NO:56) | 345000 |
| W1282X | 3 | hex | probe/DM | CGCGCCGAGGTACTGTTGCAAAGTTATTG (SEQ ID NO:57) | 327800 |
| W1282X | 3 | none | synthetic target | GATTCAATAACTTTGCAACAGTGAAGGAAAGCCTTGGAGTGATACCACAGGTGAGCAA (SEQ ID NO:58) | 683000 |
| 3849+10kbC>T | 2 | none | invader | CAAGAGTCTTCCATCTGTTGCAGTATTAAAATGAA (SEQ ID NO:59) | 390000 |
| 3849+10kbC>T | 2 | hex | probe/ER24 | ACGGACGCGGAGTGAGTAAGACACCCTGAAA (SEQ ID NO:60) | |
| 3849+10kbC>T | 2 | none | synthetic target | TTCCTTTCAGGGTGTCTTACTCACCATTTAATACTGCAACAGATGGAAGACTCTTG (SEQ ID NO:61) | 327400 |
| R553X | 4 | none | invader | CATTTACAGCAAATGCTTGCTAGACCAATAATTAGTTATTCACCTTGCTAAAGAAATTCTTGCTG (SEQ ID NO:62) | 601000 |
| R553X | 4 | hex | probe/DM | CGCGCCGAGGCATTGACCTCCACTCAGT (SEQ ID NO:63) | |
| R553X | 4 | none | synthetic target | ACTGAGTGGAGGTCAATGACCAAGAATTTCTTTAGCAAGGTGAATAACTAATTATTGGTCTAGCAAGCATTTGCTGTAAATG (SEQ ID NO:64) | |
| G542X | 4 | none | invader | TCCAAGTTTGCAGAGAAAGACAACATATAGTTCTTTC (SEQ ID NO:65) | |
| G542X | 4 | hex | probe/DM | CGCGCCGAGGGAGAAGGTGGAATCACA (SEQ ID NO:66) | |
| G542X | 4 | none | synthetic target | TGTGATTCCAACCTTCTCAAAGAACTATATTGTCTTTCTCGCAAACTTGGA (SEQ ID NO:67) | |
| 621+1G>T | 3 | none | invader | CCTTCATCACATTGGAATGCACAGTGAGAATAGCTATGTGTTTAGTTTGATTTATAAGAAGC (SEQ ID NO:68) | 664000 |
| 621+1G>T | 3 | hex | probe/DM | CGCGCCGAGGTTAATACTTCCTTGCACAGG (SEQ ID NO:69) | 311900 |
| 621+1G>T | 3 | none | synthetic target | GGGGCCTGTGCAAGGAAGTATTAACTTCTATAAATCAAACTAAACATAGAGTAAAAGGCCAA (SEQ ID NO:70) | 965000 |
| R334W | 2 | none | invader | CGCAGAACAATGCAGAATGAGAATGGTGGTGAATATTTTCCT (SEQ ID NO:71) | 467000 |
| R334W | 2 | hex | probe/DM | CGCGCCGAGGAGGAGATGATTCCTTTGATTA (SEQ ID NO:72) | 336800 |
| R334W | 2 | none | synthetic target | TGCACTAATCAAAGGAATCATCCTCTGGAAAATATTCACCACCATCTCATTCTGCATTGTTCTGCG (SEQ ID NO:73) | 703000 |

| Mutation | Pool | 3' blocking group | Oligo type (Arm) | Sequence (5'-3') | ε₂₆₀ M⁻¹ cm⁻¹ |
|---|---|---|---|---|---|
| Internal control | all | none | Invader | tgtacttcatgcgtgtctcaccacaagagagaggaggagacacaca (SEQ ID NO:74) | 503500 |
| Internal control | all | hex | Probe/SNP4b | tccgcgcgtcctcgaagaagcaccaatcatg (SEQ ID NO:75) | 321200 |
| Internal control | all | none | Synthetic Target | ttttcatgattggtgcttcatctctcttagtgtagacagcatgaagtacatt (SEQ ID NO:76) | 698200 |

| Mutation | Pool | 3' blocking group | Oligo type (Arm) | Sequence (5'-3') | |
|---|---|---|---|---|---|
| | all | Hex | DM/FAM | Y-tct-X-agc-cgg-ttt-tcc-ggc-tga-gac-ctc-ggc-gcg-hex (SEQ ID NO:77) | |
| | 1,2 | Hex | ER24/FAM | Y-tct-X-agc-cgg-ttt-tcc-ggc-tga-gac-tcc-gcg-tcc-gt-hex (SEQ ID NO:78) | |
| | all | Hex | SNP4b/Red | Y-tct-X-tcg-gcc-ttt-tcg-ccg-aga-gag-gac-gcg-cgg-a-hex (SEQ ID NO:79) | |

X = Quencher = Z28
Y = Dye = FAM for 1055-48-08 and 1055-48-09 and Y = Z35 (red) for 1055-49-04

| Mutation | Pool | 3' blocking group | Oligo type (Arm) | Sequence (5'-3') | ε₂₆₀ M⁻¹ cm⁻¹ |
|---|---|---|---|---|---|
| delF508 | delF508 | none | Invader | TGATGACGCTTCTCGTATCTATATTCATCATAGGAAACACA (SEQ ID NO:80) | 441500 |
| delF508 | delF508 | Hex | WT Probe | CGCGCCCGAGGCAAACAATAATATTTTCTTTAATGGT (SEQ ID NO:81) | 382200 |
| delF508 | delF508 | Hex | Mut Probe | AGCTGCTCCGACACACAATAATATTTTCTTTAATGGTGCCA (SEQ ID NO:82) | 418100 |
| delF508 | delF508 | Hex | DM/FAM | Y-tct-X-agc-cgg-ttt-tcc-ggc-tga-gat-gtc-gga-gat-gga-gac-ctc-ggc-gcg-hex (SEQ ID NO:83) | 347150 |
| delF508 | delF508 | Hex | Wingra/Red | Y-tct-X-tcg-gcc-ttt-tgg-ccg-gga-gct-ggg-tgt-ttc-ctat-gat-gaa-tat-aga-caga-gaa-gcg-tca-tcaaa (SEQ ID NO:84) | 390400 |
| delF508 | delF508 | none | WT Target | TGCCTGGCACCATTAAAGAAAATATCATCTTTGGTGTTTCCTATGATGAATATAGATACAGAAGCGTCATCAAA (SEQ ID NO:85) | 837500 |
| delF508 | delF508 | none | Mut Target | ATGCCTGGCACCATTAAAGAAAATATCATTGGTGTTTCCTATGATGAATATAGATACAGAAGCGTCATCAAA (SEQ ID NO:86) | 828100 |

X = Quencher = Z28
Y = Dye = FAM for 1055-48-08 and Y = Z35 (red) for 1144-16-02

| Mutation | Sample | IC ALLELE | MUT ALLELE | FOZ Ratio |
|---|---|---|---|---|
| 2789+5G>A | 26mix | 3.94 | 4.69 | 1.19 |
| R1162X | 29 | 3.42 | 2.18 | 0.62 |
| R347P | 15 | 3.38 | 4.60 | 1.36 |
| G85E | 21 | 3.62 | 2.55 | 0.70 |
| R560T | 9 | 3.30 | 2.47 | 0.75 |
| delI507 | 1 | 3.16 | 1.98 | 0.63 |
| 1898+1G>A | 111 A2/8 | 6.23 | 2.84 | 0.46 |
| R117H | 30 | 3.46 | 1.87 | 0.54 |
| delF508 homo MT | 3 | 3.44 | 1.14 | 0.33 |
| WT gDNA | 03-243 | 3.58 | 1.06 | 0.30 |
| | | | | |
| Mutation | Sample | IC ALLELE | MUT ALLELE | FOZ Ratio |
| 2184delA plasmid/internal control syn. Target | plasmid/syn. Target | 4.67 | 3.65 | 0.78 |

B

| Mutation | Sample | IC ALLELE | MUT ALLELE | FOZ Ratio |
|---|---|---|---|---|
| A455E | 8 | 3.26 | 2.88 | 0.88 |
| 3659delC | 14 | 3.38 | 2.36 | 0.68 |
| N1303K | 16 | 3.92 | 2.11 | 0.54 |
| 3120+1G>A | 6 | 3.84 | 2.45 | 0.64 |
| G551D | 20 | 3.44 | 2.04 | 0.59 |
| WT gDNA | 03-243 | 3.74 | 1.00 | 0.27 |
| I148T/Internal control | syn. target | 4.35 | 5.08 | 1.17 |
| 1078delT/Internal control | syn. target | 4.44 | 4.97 | 1.12 |

C

| Mutation | Sample | IC ALLELE | MUT ALLELE | FOZ Ratio |
|---|---|---|---|---|
| 711+1G>T | 2 | 3.95 | 2.82 | 0.71 |
| W1282X | 19 | 4.44 | 2.16 | 0.49 |
| 1717-1G>A | 28 | 4.87 | 2.19 | 0.45 |
| 3849+10kbC>T | 5 | 3.82 | 2.48 | 0.65 |
| WT gDNA | 03-243 | 4.67 | 1.10 | 0.24 |

D

| Mutation | Sample | IC ALLELE | MUT ALLELE | FOZ Ratio |
|---|---|---|---|---|
| 621+1G>T | 11 | 4.23 | 2.05 | 0.49 |
| G542X | 18 | 3.40 | 2.83 | 0.81 |
| R553X | 7 | 4.53 | 3.27 | 0.72 |
| R334W | 22 | 3.72 | 2.79 | 0.75 |
| WT gDNA | 03-243 | 4.18 | 1.14 | 0.27 |

SEQUENCE LISTING

<160> NUMBER OF SEQ ID NOS: 87

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
tttggttgtg ctgtggctcc ttggaaagtg at                32

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
cgcgccgagg atattccatg tcctattgtg                30

<210> SEQ ID NO 3
<211> LENGTH: 58
<212> TYPE: DNA
<213> ORGANISM: Artificial Sequence
<220> FEATURE:
<223> OTHER INFORMATION: Synthetic

<400> SEQUENCE: 3
caatctacac aataggacat ggaatattca ctttccaagg agccacagca caaccaaa          58

<210> SEQ ID NO 4
<211> LENGTH: 40
<212> TYPE: DNA
<213> ORGANISM: Artificial Sequence
<220> FEATURE:
<223> OTHER INFORMATION: Synthetic

<400> SEQUENCE: 4
gtttaccttc tgttggcatg tcaatgaact taaagactct                40

<210> SEQ ID NO 5
<211> LENGTH: 24

```
<212> TYPE: DNA
<213> ORGANISM: Artificial Sequence
<220> FEATURE:
<223> OTHER INFORMATION: Synthetic

<400> SEQUENCE: 5
cgcgccgagg agctcacaga tcgc                                      24

<210> SEQ ID NO 6
<211> LENGTH: 59
<212> TYPE: DNA
<213> ORGANISM: Artificial Sequence
<220> FEATURE:
<223> OTHER INFORMATION: Synthetic

<400> SEQUENCE: 6
tcagatgcga tctgtgagct gagtctttaa gttcattgac atgccaacag aaggtaaac   59

<210> SEQ ID NO 7
<211> LENGTH: 28
<212> TYPE: DNA
<213> ORGANISM: Artificial Sequence
<220> FEATURE:
<223> OTHER INFORMATION: Synthetic

<400> SEQUENCE: 7
cagggaaatt gccgagtgac cgccatgt                                  28

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
acggacgcgg agggcagaac aatgcag                                   27

<210> SEQ ID NO 9
<211> LENGTH: 50
<212> TYPE: DNA
<213> ORGANISM: Artificial Sequence
<220> FEATURE:
<223> OTHER INFORMATION: Synthetic

<400> SEQUENCE: 9
ctcattctgc attgttctgc ccatggcggt cactcggcaa tttccctggg           50

<210> SEQ ID NO 10
<211> LENGTH: 54
<212> TYPE: DNA
<213> ORGANISM: Artificial Sequence
<220> FEATURE:
<223> OTHER INFORMATION: Synthetic

<400> SEQUENCE: 10
gactctcctt ttggatacct agatgtttta acagaaaaag aaatatttga aagt       54

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
```
cgcgccgagg atatgttctt tgaataacctt acttat                                36

<210> SEQ ID NO 12
<211> LENGTH: 79
<212> TYPE: DNA
<213> ORGANISM: Artificial Sequence
<220> FEATURE:
<223> OTHER INFORMATION: Synthetic

<400> SEQUENCE: 12
ataagtaagg tattcaaaga acatatcttt caaatatttc ttttctgtt aaaacatcta     60 ggtatccaaa aggagagtc                                                 79

<210> SEQ ID NO 13
<211> LENGTH: 38
<212> TYPE: DNA
<213> ORGANISM: Artificial Sequence
<220> FEATURE:
<223> OTHER INFORMATION: Synthetic

<400> SEQUENCE: 13
ccccaaactc tccagtctgt ttaaaaaatt gtttttc                              38

<210> SEQ ID NO 14
<211> LENGTH: 38
<212> TYPE: DNA
<213> ORGANISM: Artificial Sequence
<220> FEATURE:
<223> OTHER INFORMATION: Synthetic

<400> SEQUENCE: 14
ccccaaactc tccagtctgt ttaaaagatt attttttc                             38

<210> SEQ ID NO 15
<211> LENGTH: 28
<212> TYPE: DNA
<213> ORGANISM: Artificial Sequence
<220> FEATURE:
<223> OTHER INFORMATION: Synthetic

<400> SEQUENCE: 15
cgcgccgagg gtttctgtcc aggagaca                                        28

<210> SEQ ID NO 16
<211> LENGTH: 47
<212> TYPE: DNA
<213> ORGANISM: Artificial Sequence
<220> FEATURE:
<223> OTHER INFORMATION: Synthetic

<400> SEQUENCE: 16
gctttgatga cgcttctgta tctatattca tcataggaaa caccaat                   47

<210> SEQ ID NO 17
<211> LENGTH: 32
<212> TYPE: DNA
<213> ORGANISM: Artificial Sequence
<220> FEATURE:
<223> OTHER INFORMATION: Synthetic

<400> SEQUENCE: 17
cgcgccgagg agatattttc tttaatggtg cc                                   32

<210> SEQ ID NO 18
<211> LENGTH: 77

<212> TYPE: DNA
<213> ORGANISM: Artificial Sequence
<220> FEATURE:
<223> OTHER INFORMATION: Synthetic

<400> SEQUENCE: 18
gcctggcacc attaaagaaa atatctttgg tgtttcctat gatgaatata gatacagaag    60
cgtcatcaaa gcatgcc    77

<210> SEQ ID NO 19
<211> LENGTH: 41
<212> TYPE: DNA
<213> ORGANISM: Artificial Sequence
<220> FEATURE:
<223> OTHER INFORMATION: Synthetic

<400> SEQUENCE: 19
gcccttcggc gatgtttttt ctggagattt atgttctatg t    41

<210> SEQ ID NO 20
<211> LENGTH: 37
<212> TYPE: DNA
<213> ORGANISM: Artificial Sequence
<220> FEATURE:
<223> OTHER INFORMATION: Synthetic

<400> SEQUENCE: 20
acggacgcgg agaaatcttt ttatatttag gggtaag    37

<210> SEQ ID NO 21
<211> LENGTH: 74
<212> TYPE: DNA
<213> ORGANISM: Artificial Sequence
<220> FEATURE:
<223> OTHER INFORMATION: Synthetic

<400> SEQUENCE: 21
agatccttac ccctaaatat aaaagatttc atagaacat aaatctccag aaaaaacatc    60
gccgaagggc atta    74

<210> SEQ ID NO 22
<211> LENGTH: 39
<212> TYPE: DNA
<213> ORGANISM: Artificial Sequence
<220> FEATURE:
<223> OTHER INFORMATION: Synthetic

<400> SEQUENCE: 22
aatcatagct tcctatgacc cggataacaa ggaggaact    39

<210> SEQ ID NO 23
<211> LENGTH: 29
<212> TYPE: DNA
<213> ORGANISM: Artificial Sequence
<220> FEATURE:
<223> OTHER INFORMATION: Synthetic

<400> SEQUENCE: 23
cgcgccgagg actctatcgc gatttatct    29

<210> SEQ ID NO 24
<211> LENGTH: 63
<212> TYPE: DNA
<213> ORGANISM: Artificial Sequence
<220> FEATURE:

<223> OTHER INFORMATION: Synthetic

<400> SEQUENCE: 24
atgcctagat aaatcgcgat agagtgttcc tccttgttat ccgggtcata ggaagctatg    60
att                                                                 63

<210> SEQ ID NO 25
<211> LENGTH: 53
<212> TYPE: DNA
<213> ORGANISM: Artificial Sequence
<220> FEATURE:
<223> OTHER INFORMATION: Synthetic

<400> SEQUENCE: 25
catgaatgac atttacagca aatgcttgct agaccaataa ttagttattc act          53

<210> SEQ ID NO 26
<211> LENGTH: 33
<212> TYPE: DNA
<213> ORGANISM: Artificial Sequence
<220> FEATURE:
<223> OTHER INFORMATION: Synthetic

<400> SEQUENCE: 26
acggacgcgg aggttgctaa agaaattctt gct                                33

<210> SEQ ID NO 27
<211> LENGTH: 83
<212> TYPE: DNA
<213> ORGANISM: Artificial Sequence
<220> FEATURE:
<223> OTHER INFORMATION: Synthetic

<400> SEQUENCE: 27
caacgagcaa gaatttcttt agcaacgtga ataactaatt attggtctag caagcatttg    60
ctgtaaatgt cattcatgta aaa                                            83

<210> SEQ ID NO 28
<211> LENGTH: 49
<212> TYPE: DNA
<213> ORGANISM: Artificial Sequence
<220> FEATURE:
<223> OTHER INFORMATION: Synthetic

<400> SEQUENCE: 28
gcaattttgg atgaccttct gcctcttacc atatttgact tcatccagt               49

<210> SEQ ID NO 29
<211> LENGTH: 34
<212> TYPE: DNA
<213> ORGANISM: Artificial Sequence
<220> FEATURE:
<223> OTHER INFORMATION: Synthetic

<400> SEQUENCE: 29
cgcgccgagg atatgtaaaa ataagtaccg ttaa                               34

<210> SEQ ID NO 30
<211> LENGTH: 86
<212> TYPE: DNA
<213> ORGANISM: Artificial Sequence
<220> FEATURE:
<223> OTHER INFORMATION: Synthetic

<400> SEQUENCE: 30

```
agacatactt aacggtactt atttttacat atctggatga agtcaaatat ggtaagaggc     60
agaaggtcat ccaaaattgc tatatc                                         86

<210> SEQ ID NO 31
<211> LENGTH: 36
<212> TYPE: DNA
<213> ORGANISM: Artificial Sequence
<220> FEATURE:
<223> OTHER INFORMATION: Synthetic

<400> SEQUENCE: 31
gagagttggc cattcttgta tggtttggtt gacttt                              36

<210> SEQ ID NO 32
<211> LENGTH: 30
<212> TYPE: DNA
<213> ORGANISM: Artificial Sequence
<220> FEATURE:
<223> OTHER INFORMATION: Synthetic

<400> SEQUENCE: 32
cgcgccgagg gtaggtttac cttctgttgg                                     30

<210> SEQ ID NO 33
<211> LENGTH: 59
<212> TYPE: DNA
<213> ORGANISM: Artificial Sequence
<220> FEATURE:
<223> OTHER INFORMATION: Synthetic

<400> SEQUENCE: 33
catgccaaca gaaggtaaac ctacaagtca accaaaccat acaagaatgg ccaactctc      59

<210> SEQ ID NO 34
<211> LENGTH: 45
<212> TYPE: DNA
<213> ORGANISM: Artificial Sequence
<220> FEATURE:
<223> OTHER INFORMATION: Synthetic

<400> SEQUENCE: 34
cctgaaagat attaatttca agatagaaag aggacagttg ttggt                    45

<210> SEQ ID NO 35
<211> LENGTH: 27
<212> TYPE: DNA
<213> ORGANISM: Artificial Sequence
<220> FEATURE:
<223> OTHER INFORMATION: Synthetic

<400> SEQUENCE: 35
acggacgcgg agaggttgct ggatcca                                        27

<210> SEQ ID NO 36
<211> LENGTH: 63
<212> TYPE: DNA
<213> ORGANISM: Artificial Sequence
<220> FEATURE:
<223> OTHER INFORMATION: Synthetic

<400> SEQUENCE: 36
ccagtggatc cagcaacctc caacaactgt cctctttcta tcttgaaatt aatatctttc     60
agg                                                                  63
```

<210> SEQ ID NO 37
<211> LENGTH: 34
<212> TYPE: DNA
<213> ORGANISM: Artificial Sequence
<220> FEATURE:
<223> OTHER INFORMATION: Synthetic

<400> SEQUENCE: 37
agtgcatagg gaagcacaga taaaaacacc acat                                      34

<210> SEQ ID NO 38
<211> LENGTH: 29
<212> TYPE: DNA
<213> ORGANISM: Artificial Sequence
<220> FEATURE:
<223> OTHER INFORMATION: Synthetic

<400> SEQUENCE: 38
cgcgccgagg agaaccctga gaagaagaa                                            29

<210> SEQ ID NO 39
<211> LENGTH: 56
<212> TYPE: DNA
<213> ORGANISM: Artificial Sequence
<220> FEATURE:
<223> OTHER INFORMATION: Synthetic

<400> SEQUENCE: 39
agccttcttc ttctcagggt tcttgtggtg tttttatctg tgcttcccta tgcact             56

<210> SEQ ID NO 40
<211> LENGTH: 53
<212> TYPE: DNA
<213> ORGANISM: Artificial Sequence
<220> FEATURE:
<223> OTHER INFORMATION: Synthetic

<400> SEQUENCE: 40
gcagagaaag acaatatagt tcttggagaa ggtggaatca cactgagtgg agt                53

<210> SEQ ID NO 41
<211> LENGTH: 30
<212> TYPE: DNA
<213> ORGANISM: Artificial Sequence
<220> FEATURE:
<223> OTHER INFORMATION: Synthetic

<400> SEQUENCE: 41
cgcgccgagg atcaacgagc aagaatttct                                           30

<210> SEQ ID NO 42
<211> LENGTH: 86
<212> TYPE: DNA
<213> ORGANISM: Artificial Sequence
<220> FEATURE:
<223> OTHER INFORMATION: Synthetic

<400> SEQUENCE: 42
cttgctaaag aaattcttgc tcgttgatct ccactcagtg tgattccacc ttctccaaga         60
actatattgt ctttctctgc aaactt                                              86

<210> SEQ ID NO 43
<211> LENGTH: 39
<212> TYPE: DNA
<213> ORGANISM: Artificial Sequence

```
<220> FEATURE:
<223> OTHER INFORMATION: Synthetic

<400> SEQUENCE: 43
aaatcaaact aaacatagct attctcatct gcattccat                                  39

<210> SEQ ID NO 44
<211> LENGTH: 29
<212> TYPE: DNA
<213> ORGANISM: Artificial Sequence
<220> FEATURE:
<223> OTHER INFORMATION: Synthetic

<400> SEQUENCE: 44
acggacgcgg aggtgtgatg aaggccaaa                                             29

<210> SEQ ID NO 45
<211> LENGTH: 60
<212> TYPE: DNA
<213> ORGANISM: Artificial Sequence
<220> FEATURE:
<223> OTHER INFORMATION: Synthetic

<400> SEQUENCE: 45
ccattttggg ccttcatcac actggaatgc agatgagaat agctatgttt agtttgattt          60

<210> SEQ ID NO 46
<211> LENGTH: 40
<212> TYPE: DNA
<213> ORGANISM: Artificial Sequence
<220> FEATURE:
<223> OTHER INFORMATION: Synthetic

<400> SEQUENCE: 46
ccatatttct tgatcactcc actgttcata gggatccaat                                 40

<210> SEQ ID NO 47
<211> LENGTH: 35
<212> TYPE: DNA
<213> ORGANISM: Artificial Sequence
<220> FEATURE:
<223> OTHER INFORMATION: Synthetic

<400> SEQUENCE: 47
cgcgccgagg cttttttcta aatgttccag aaaaa                                      35

<210> SEQ ID NO 48
<211> LENGTH: 74
<212> TYPE: DNA
<213> ORGANISM: Artificial Sequence
<220> FEATURE:
<223> OTHER INFORMATION: Synthetic

<400> SEQUENCE: 48
atttattttt tctggaacat ttagaaaaaa gttggatccc tatgaacagt ggagtgatca          60
agaaatatgg aaag                                                            74

<210> SEQ ID NO 49
<211> LENGTH: 61
<212> TYPE: DNA
<213> ORGANISM: Artificial Sequence
<220> FEATURE:
<223> OTHER INFORMATION: Synthetic

<400> SEQUENCE: 49
```

```
gcctttccag ttgtataatt tataacaata gtgcctaaaa gattaaatca ataggtacat    60
t                                                                    61
```

<210> SEQ ID NO 50
<211> LENGTH: 33
<212> TYPE: DNA
<213> ORGANISM: Artificial Sequence
<220> FEATURE:
<223> OTHER INFORMATION: Synthetic

<400> SEQUENCE: 50

```
acggacgcgg agaattcatc aaatttgttc agg                                 33
```

<210> SEQ ID NO 51
<211> LENGTH: 32
<212> TYPE: DNA
<213> ORGANISM: Artificial Sequence
<220> FEATURE:
<223> OTHER INFORMATION: Synthetic

<400> SEQUENCE: 51

```
cgcgccgagg aattcatcaa atttgttcag gt                                  32
```

<210> SEQ ID NO 52
<211> LENGTH: 82
<212> TYPE: DNA
<213> ORGANISM: Artificial Sequence
<220> FEATURE:
<223> OTHER INFORMATION: Synthetic

<400> SEQUENCE: 52

```
acctgaacaa atttgatgaa ttatgtacct attgatttaa tcttttaggc actattgtta    60
taaattatac aactggaaag gc                                             82
```

<210> SEQ ID NO 53
<211> LENGTH: 63
<212> TYPE: DNA
<213> ORGANISM: Artificial Sequence
<220> FEATURE:
<223> OTHER INFORMATION: Synthetic

<400> SEQUENCE: 53

```
gcctttcaaa ttcagattga gcatactaaa agtgactctc taattttcta tttttggtaa    60
tat                                                                  63
```

<210> SEQ ID NO 54
<211> LENGTH: 28
<212> TYPE: DNA
<213> ORGANISM: Artificial Sequence
<220> FEATURE:
<223> OTHER INFORMATION: Synthetic

<400> SEQUENCE: 54

```
cgcgccgagg agacatctcc aagtttgc                                       28
```

<210> SEQ ID NO 55
<211> LENGTH: 89
<212> TYPE: DNA
<213> ORGANISM: Artificial Sequence
<220> FEATURE:
<223> OTHER INFORMATION: Synthetic

<400> SEQUENCE: 55

```
ctctgcaaac ttggagatgt cttattacca aaaatagaaa attagagagt cactttagt    60
```
atgctcaatc tgaatttgaa aggcacatc                                89

<210> SEQ ID NO 56
<211> LENGTH: 34
<212> TYPE: DNA
<213> ORGANISM: Artificial Sequence
<220> FEATURE:
<223> OTHER INFORMATION: Synthetic

<400> SEQUENCE: 56
gctcacctgt ggtatcactc caaaggcttt ccta                          34

<210> SEQ ID NO 57
<211> LENGTH: 30
<212> TYPE: DNA
<213> ORGANISM: Artificial Sequence
<220> FEATURE:
<223> OTHER INFORMATION: Synthetic

<400> SEQUENCE: 57
cgcgccgagg tcactgttgc aaagttattg                               30

<210> SEQ ID NO 58
<211> LENGTH: 59
<212> TYPE: DNA
<213> ORGANISM: Artificial Sequence
<220> FEATURE:
<223> OTHER INFORMATION: Synthetic

<400> SEQUENCE: 58
gattcaataa ctttgcaaca gtgaaggaaa gcctttggag tgataccaca ggtgagcaa    59

<210> SEQ ID NO 59
<211> LENGTH: 35
<212> TYPE: DNA
<213> ORGANISM: Artificial Sequence
<220> FEATURE:
<223> OTHER INFORMATION: Synthetic

<400> SEQUENCE: 59
caagagtctt ccatctgttg cagtattaaa atgga                         35

<210> SEQ ID NO 60
<211> LENGTH: 31
<212> TYPE: DNA
<213> ORGANISM: Artificial Sequence
<220> FEATURE:
<223> OTHER INFORMATION: Synthetic

<400> SEQUENCE: 60
acggacgcgg agtgagtaag acaccctgaa a                             31

<210> SEQ ID NO 61
<211> LENGTH: 29
<212> TYPE: DNA
<213> ORGANISM: Artificial Sequence
<220> FEATURE:
<223> OTHER INFORMATION: Synthetic

<400> SEQUENCE: 61
cgcgccgagg tgagtaagac accctgaaa                                29

<210> SEQ ID NO 62
<211> LENGTH: 57
<212> TYPE: DNA

<213> ORGANISM: Artificial Sequence
<220> FEATURE:
<223> OTHER INFORMATION: Synthetic

<400> SEQUENCE: 62
ttcctttcag ggtgtcttac tcaccatttt aatactgcaa cagatggaag actcttg    57

<210> SEQ ID NO 63
<211> LENGTH: 65
<212> TYPE: DNA
<213> ORGANISM: Artificial Sequence
<220> FEATURE:
<223> OTHER INFORMATION: Synthetic

<400> SEQUENCE: 63
catttacagc aaatgcttgc tagaccaata attagttatt caccttgcta aagaaattct    60
tgctg    65

<210> SEQ ID NO 64
<211> LENGTH: 28
<212> TYPE: DNA
<213> ORGANISM: Artificial Sequence
<220> FEATURE:
<223> OTHER INFORMATION: Synthetic

<400> SEQUENCE: 64
cgcgccgagg cattgacctc cactcagt    28

<210> SEQ ID NO 65
<211> LENGTH: 82
<212> TYPE: DNA
<213> ORGANISM: Artificial Sequence
<220> FEATURE:
<223> OTHER INFORMATION: Synthetic

<400> SEQUENCE: 65
actgagtgga ggtcaatgag caagaatttc tttagcaagg tgaataacta attattggtc    60
tagcaagcat ttgctgtaaa tg    82

<210> SEQ ID NO 66
<211> LENGTH: 35
<212> TYPE: DNA
<213> ORGANISM: Artificial Sequence
<220> FEATURE:
<223> OTHER INFORMATION: Synthetic

<400> SEQUENCE: 66
tccaagtttg cagagaaaga caatatagtt ctttc    35

<210> SEQ ID NO 67
<211> LENGTH: 27
<212> TYPE: DNA
<213> ORGANISM: Artificial Sequence
<220> FEATURE:
<223> OTHER INFORMATION: Synthetic

<400> SEQUENCE: 67
cgcgccgagg gagaaggtgg aatcaca    27

<210> SEQ ID NO 68
<211> LENGTH: 51
<212> TYPE: DNA
<213> ORGANISM: Artificial Sequence
<220> FEATURE:
<223> OTHER INFORMATION: Synthetic

<400> SEQUENCE: 68
tgtgattcca ccttctcaaa gaactatatt gtctttctct gcaaacttgg a          51

<210> SEQ ID NO 69
<211> LENGTH: 59
<212> TYPE: DNA
<213> ORGANISM: Artificial Sequence
<220> FEATURE:
<223> OTHER INFORMATION: Synthetic

<400> SEQUENCE: 69
ccttcatcac attggaatgc agatgagaat agctatgttt agtttgattt ataagaagc   59

<210> SEQ ID NO 70
<211> LENGTH: 30
<212> TYPE: DNA
<213> ORGANISM: Artificial Sequence
<220> FEATURE:
<223> OTHER INFORMATION: Synthetic

<400> SEQUENCE: 70
cgcgccgagg ttaatacttc cttgcacagg                                  30

<210> SEQ ID NO 71
<211> LENGTH: 86
<212> TYPE: DNA
<213> ORGANISM: Artificial Sequence
<220> FEATURE:
<223> OTHER INFORMATION: Synthetic

<400> SEQUENCE: 71
ggggcctgtg caaggaagta ttaacttctt ataaatcaaa ctaaacatag ctattctcat  60
ctgcattcca atgtgatgaa ggccaa                                      86

<210> SEQ ID NO 72
<211> LENGTH: 41
<212> TYPE: DNA
<213> ORGANISM: Artificial Sequence
<220> FEATURE:
<223> OTHER INFORMATION: Synthetic

<400> SEQUENCE: 72
cgcagaacaa tgcagaatga gatggtggtg aatattttcc t                     41

<210> SEQ ID NO 73
<211> LENGTH: 31
<212> TYPE: DNA
<213> ORGANISM: Artificial Sequence
<220> FEATURE:
<223> OTHER INFORMATION: Synthetic

<400> SEQUENCE: 73
cgcgccgagg agaggatgat tcctttgatt a                                31

<210> SEQ ID NO 74
<211> LENGTH: 66
<212> TYPE: DNA
<213> ORGANISM: Artificial Sequence
<220> FEATURE:
<223> OTHER INFORMATION: Synthetic

<400> SEQUENCE: 74
tgcactaatc aaaggaatca tcctctggaa aatattcacc accatctcat tctgcattgt  60
tctgcg 66

<210> SEQ ID NO 75
<211> LENGTH: 44
<212> TYPE: DNA
<213> ORGANISM: Artificial Sequence
<220> FEATURE:
<223> OTHER INFORMATION: Synthetic

<400> SEQUENCE: 75
tgtacttcat gctgtctaca ctaagagaga atgagagaca caca 44

<210> SEQ ID NO 76
<211> LENGTH: 30
<212> TYPE: DNA
<213> ORGANISM: Artificial Sequence
<220> FEATURE:
<223> OTHER INFORMATION: Synthetic

<400> SEQUENCE: 76
tccgcgcgtc ctgaagaagc accaatcatg 30

<210> SEQ ID NO 77
<211> LENGTH: 68
<212> TYPE: DNA
<213> ORGANISM: Artificial Sequence
<220> FEATURE:
<223> OTHER INFORMATION: Synthetic

<400> SEQUENCE: 77
tttcatgatt ggtgcttctt cagtgtgtct ctcattctct cttagtgtag acagcatgaa 60
gtacattt 68

<210> SEQ ID NO 78
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 78
tctagccggt tttccggctg agacctcggc gcg 33

<210> SEQ ID NO 79
<211> LENGTH: 35
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 79
tctagccggt tttccggctg agactccgcg tccgt 35

<210> SEQ ID NO 80
<211> LENGTH: 34
<212> TYPE: DNA
<213> ORGANISM: Artificial Sequence

```
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 80
tcttcggcct tttggccgag agaggacgcg cgga                                    34

<210> SEQ ID NO 81
<211> LENGTH: 40
<212> TYPE: DNA
<213> ORGANISM: Artificial Sequence
<220> FEATURE:
<223> OTHER INFORMATION: Synthetic

<400> SEQUENCE: 81
tgatgacgct tctgtatcta tattcatcat aggaaacaca                              40

<210> SEQ ID NO 82
<211> LENGTH: 35
<212> TYPE: DNA
<213> ORGANISM: Artificial Sequence
<220> FEATURE:
<223> OTHER INFORMATION: Synthetic

<400> SEQUENCE: 82
cgcgccgagg caaagatgat attttcttta atggt                                   35

<210> SEQ ID NO 83
<211> LENGTH: 39
<212> TYPE: DNA
<213> ORGANISM: Artificial Sequence
<220> FEATURE:
<223> OTHER INFORMATION: Synthetic

<400> SEQUENCE: 83
agctcgtccg acacaataat attttcttta atggtgcca                               39

<210> SEQ ID NO 84
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 84
tctagccggt tttccggctg agacctcggc gcg                                     33

<210> SEQ ID NO 85
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: The residue at this position is linked to a Z28
      quenching group.

<400> SEQUENCE: 85
```

```
tcttcggcct tttggccgag agatgtcgga cgagct                          36

<210> SEQ ID NO 86
<211> LENGTH: 74
<212> TYPE: DNA
<213> ORGANISM: Artificial Sequence
<220> FEATURE:
<223> OTHER INFORMATION: Synthetic

<400> SEQUENCE: 86
tgcctggcac cattaaagaa aatatcatct ttggtgtttc ctatgatgaa tatagataca  60
gaagcgtcat caaa                                                   74

<210> SEQ ID NO 87
<211> LENGTH: 72
<212> TYPE: DNA
<213> ORGANISM: Artificial Sequence
<220> FEATURE:
<223> OTHER INFORMATION: Synthetic

<400> SEQUENCE: 87
atgcctggca ccattaaaga aaatatcatt ggtgtttcct atgatgaata tagatacaga  60
agcgtcatca aa                                                     72
```

CFTR ALLELE DETECTION ASSAYS

The present Application claims priority to U.S. Provisional Application Ser. No. 60/426,144, filed Nov. 14, 2002, herein incorporated by reference.

FIELD OF THE INVENTION

The present invention relates to compositions and methods for the detection and characterization of mutations associated with cystic fibrosis. More particularly, the present invention relates to compositions, methods and kits for using invasive cleavage structure assays (e.g. the INVADER assay) to screen nucleic acid samples, e.g., from patients, for the presence of any one of a collection of mutations in the CFTR gene associated with cystic fibrosis. The present invention also relates to compositions, methods and kits for screening sets of CFTR alleles in a single reaction container.

BACKGROUND OF THE INVENTION

Cystic fibrosis (CF) is the most predominant lethal autosomal recessive genetic disorder in Caucasians, with affected individuals occurring in approximately 1/3,000 live births; incidence is lower in other ethnic groups (Heim, et al., Genetics in Medicine 3(3):168-176 (2001)). CF disease is associated with high morbidity and reduced life span. Individuals carrying two defective CF chromosomes typically display a panoply of symptoms, including sinopulmonary disease, pancreatic insufficiency, and male infertility. Certain bacterial infections, e.g. *Pseudomonas aeruginosa*, are typically found only in individuals affected by CF (Raman, et al., Pediatrics 109(1): E13 (2002)). CFTR mutations are implicated in a broad spectrum of diseases such as congenital bilateral absence of the vas deference (CBAVD) (Dumur, et al., Hum Genet 97: 7-10 (1996)), allergic bronchopulmonary aspergillosis, and isolated chronic pancreatitis (Raman, supra). Moreover, disease manifestations may be exacerbated in some cases by additional environmental risk factors such as smoking, alcohol consumption, or allergy (Raman, supra).

Approximately one in 25 to 30 Caucasians is a CF carrier (Grody, Cutting, et al., Genetics in Medicine 3(2):149-154 (2001)); however, no noticeable defects or biochemical or physiological alterations can be readily used to ascertain carrier status (Grody and Desnick, Genetics in Medicine 3(2):87-90 (2001)). Determination of carrier status, as well as confirmation of CF disease, may be of value in genetic counseling as well as in early diagnosis to determine treatment and disease management (Grody and Desnick, supra). There is currently no cure for the disease, although recent advances in palliative treatments have dramatically improved the quality of life and overall longevity of affected individuals.

Diagnosis of CF has been accomplished using various means since the 1950's and often requires positive results obtained using more than one clinical parameter (Rosenstein and Cutting, Journal of Pediatrics 132(4): 589-595 (1998)). In some cases, definitive diagnosis can remain elusive for years (Rosenstein and Cutting, supra). Sweat chloride testing, involving measurement of chloride in sweat following iontophoresis of pilocarpineis a widely used procedure, although there are reports of CF affected individuals with normal sweat chloride levels, even upon repeat testing (LeGrys, Laboratory Medicine 33(1): 55-57 (2002)). Nasal potential difference, involving bioelectrical measurements of the nasal epithelium, is another clinical method that has been used to detect CF in individuals with normal sweat chloride levels (Wilson, et al., Journal of Pediatrics 132 (4): 596-599 (1998)). Immunoreactive trypsinogen (IRT) levels have been used alone as well as in combination with mutational analysis for neonatal analysis (Gregg, et al., Pediatrics 99(6): 819-824 (1997)). Elevated IRT levels are suggestive of CF disease, although the IRT assay alone has low positive predictive value, often requires repeat testing (Gregg, et al., supra), and is complicated by age-related declines in IRT values beyond 30 days (Rock, et al., Pediatrics 85(6): 1001-1007 (1990)).

The CFTR gene was first identified in 1989. The gene is located on chromosome 7, includes 27 exons, and spans 250kb (Kerem, et al., Science 245: 1073-1080 (1989); Riordan, et al., Science 245: 1066-1073 (1989); Rommens, et al., Science 245: 1059-1065 (1989)). CFTR encodes a chloride ion channel; defect-causing lesions in the gene result in abnormal intracellular chloride levels, leading to thickened mucosal secretions, which in turn affect multiple organ systems. More than 950 mutations have been identified in the cystic fibrosis transmembrane conductance regulator (CFTR) gene (ref CFGAC). One mutation, $\Delta$F508, causes the loss of a phenylalanine residue at amino acid 508 in CFTR gene product and accounts for 66% of defective CF chromosomes worldwide (Bobadilla, et al., Human Mutation 19: 575-606 (2002)). The remaining alleles exhibit considerable ethnic and regional heterogeneity (Bobadilla, et al., supra) and, in many cases, exhibit poor genotype-phenotype correlations (Grody, Cutting et al., supra). Severity of CF disease in individuals affected by more rare mutations is highly variable. In some cases, a typical, moderate, or partial CF disease may be the result of a partially functional CFTR gene product (Noone and Knowles, Respiratory Research 2(6):328-332 (2001)).

The identification of the CFTR gene enabled significant advances in CF diagnosis and carrier screening. However, use of genetics to establish carrier status or the presence of CF disease remains challenging for several reasons. First, the number of exons and the overall size of the CFTR gene complicate analysis. Most methods applied to CF testing rely on PCR to amplify the more than 15 different exons and intronic regions found thus far to contain the most frequently encountered mutations; the amplicons are then tested individually to determine which mutations, if any, are present. Second, the number of mutations identified in the CFTR gene has increased steadily. As recently as 1994, 400 mutations had been identified; that number grew to more than 950 by 2002 ((Cystic Fibrosis Genetic Analysis Consortium (CFGAC) 2002) and is likely to continue to increase. The existence of so many distinct alleles complicates the use of a number of standard mutation detection methods such as PCR-RFLP or AS-PCR. Third, many of rarely encountered alleles appear to exhibit incomplete penetrance (Grody, Cutting et al. supra) and may be associated with heterologous genetic alterations (Raman, et al., supra; Rohlfs, et al., Genetics in Medicine 4(5):319-323 (2002)). Fourth, some alleles, such as R117H, produce different phenotypes depending on chromosomal background (Kiesewetter, et al., Nature Genetics 5(3): 274-278 (1993)). Despite these challenges, widespread genetic screening for CF has been recommended for Caucasian and Ashkenazi Jewish couples and made available to other ethnic groups in the U.S. considering pregnancy or already expecting (Grody, Cutting et al. supra). The American College of Obstetrics and Gynecology (ACOG), the American College of Medical Genetics (AMCG), and the National Center for Human Genomics Research (NCHGR) of the NIH have together agreed upon an initial panel of 25 mutations commonly found in North America, including (F508, to be used for prenatal and carrier screening in the US (Grody, Cutting et al. supra). This panel is more inclusive for mutations affecting certain ethnic groups than some others, particularly Ashkenazi Jews and Caucasians of North European, non-Jewish descent. Nonetheless, the joint committee concluded that all couples seeking to have a child could benefit from screening that would identify, at a minimum, 50-65% of CFTR mutations. Future recommendations will likely expand the core collection of alleles to be screened in order to encompass a greater percentage of the alleles found in other sub-populations.

The case of the most commonly encountered CF allele, ΔF508, presents a particular challenge to nucleic acid-based detection methods. This region contains three polymorphisms that do not cause CF but may interfere with hybridization of wild type probes (Grody, Cutting et al. 2001). These variations result in the following amino acid changes: F508C, I507V and I506V. This situation is complicated by the existence of the CF-causing mutation ΔI507. Many methods applied to CF genotyping rely on the use of reflex tests to distinguish these benign polymorphisms from the CF-causing mutations in codons 507 and 508. Assays that rely primarily on the stringency of annealing of an oligonucleotide to a target sequence, e.g. PCR, SBH can yield false positive or negative results in the presence of such polymorphisms (Fujimura, Northrup et al. 1990).

What is needed are detection assays that may be applied directly to the analysis of CTFR sequences (e.g. genomic sequences), as well as assays capable of detecting multiple CTFR alleles in a single reaction vessel.

SUMMARY OF THE INVENTION

The present invention provides compositions and methods for the detection and characterization of mutations associated with cystic fibrosis. More particularly, the present invention provides compositions, methods and kits for using invasive cleavage structure assays (e.g. the INVADER assay) to screen nucleic acid samples, e.g., from patients, for the presence of any one of a collection of mutations in the CFTR gene associated with cystic fibrosis. The present invention also provides compositions, methods and kits for screening sets of CFTR alleles in a single reaction container.

In other embodiments, synthetic DNA suitable for use with the methods and compositions of the present invention is made using a purified polymerase on multiply-primed genomic DNA, as provided, e.g., in U.S. Pat. Nos. 6,291, 187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ29 polymerase (as described, e.g., in U.S. Pat. Nos. 5,198,543 and 5,001,050, each herein incorporated by reference in their entireties for all purposes) in combination with exonuclease-resistant random primers, such as hexamers.

The method is not limited by the nature of the target nucleic acid. In some embodiments, the target nucleic acid is single stranded or double stranded DNA or RNA. In some embodiments, double stranded nucleic acid is rendered single stranded (e.g., by heat) prior to formation of the cleavage structure. In some embodiments, the source of target nucleic acid comprises a sample containing genomic DNA. Sample include, but are not limited to, blood, saliva, cerebral spinal fluid, pleural fluid, milk, lymph, sputum and semen.

In some embodiments, the target nucleic acid comprises genomic DNA or mRNA. In other embodiments, the target nucleic acid comprises synthetic DNA or RNA. In some preferred embodiments, synthetic DNA or RNA within a sample is created using a purified polymerase. In some preferred embodiments, creation of synthetic DNA using a purified polymerase comprises the use of PCR. In some preferred embodiments, creation of synthetic DNA comprises use of the methods and compositions for amplification using RNA-DNA composite primers (e.g., as disclosed in U.S. Pat. No. 6,251,639, herein incorporated by reference in its entirety). In other preferred embodiments, creation of synthetic DNA using a purified DNA polymerase suitable for use with the methods of the present invention comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises amplification using nucleic acids comprising loop-forming sequences, e.g., as described in U.S. Pat. No. 6,410,278, herein incorporated by reference in its entirety.

In some preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197,557, issued Mar. 6, 2001, and in PCT application WO 98/39485, each incorporated by reference herein in their entireties for all purposes.

The pooled detection assays for detection of mutations in the CFTR gene provided in the present invention may find use in detection assays that include, but are not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); rolling circle replication (e.g., U.S. Pat. Nos. 6,210,884, 6,183,960 and 6,235,502, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); and sandwich hybridization methods (e.g., U.S. Pat. No. 5,288,609, herein incorporated by reference in its entirety).

In some embodiments, the present invention provides kits or compositions comprising a non-amplified oligonucleotide detection assay configured for detecting at least one CFTR allele. In other embodiments, the non-amplified oligonucleotide detection assay comprises first and second oligonucleotides configured to form an invasive cleavage structure (e.g. an INVADER assay) in combination with a target sequence comprising said at least one CFTR allele. In particular embodiments, the first oligonucleotide comprises a 5' portion and a 3' portion, wherein the 3' portion is configured to hybridize to the target sequence, and wherein the 5' portion is configured to not hybridize to the target sequence. In other embodiments, the second oligonucleotide comprises a 5' portion and a 3' portion, wherein the 5' portion is configured to hybridize to the target sequence, and wherein the 3' portion is configured to not hybridize to the target sequence.

In some embodiments, the at least one CFTR allele is selected from the group consisting of 2789+5G>A, R1162X, R560T, 1898+1G>A, delI507, I148T, A455E, or the wild-type versions thereof. In other embodiments, the at least one CFTR allele comprises 2789+5G>A, R1162X, R560T, 1898+1G>A, delI507, I148T, and A455E.

In additional embodiments, the at least one CFTR allele is selected from the group consisting of 3120+1G>A, 3659delC, G551 D, N1303K, 1078delT, R334W, 711+1G>T, 3849+10kb, or the wild-type versions thereof. In certain embodiments, the at least one CFTR allele comprises 3120+1G>A, 3659delC, G551D, N1303K, 1078delT, R334W, 711+1G>T, and 3849+10kb.

In other embodiments, the at least one CFTR allele is selected from the group consisting of 621+1G>T, W1282X, 1717-1G>A, R117H, or the wild-type versions thereof. In some embodiments, the at least one CFTR allele comprises 621+1G>T, W1282X, 1717-1G>A, and R117H.

In particular embodiments, the at least one CFTR allele is selected from the group consisting of R347P, G85E, 2184delA, G542X, R553X, or the wild-type versions thereof. In other embodiments, the at least one CFTR allele comprises R347P, G85E, 2184delA, G542X, and R553X. In still other embodiments, the at least one CFTR allele comprises R347P, G85E, G542X, R553X.

In some embodiments, the at least one CFTR allele comprises 2184delA or the wild-type version thereof. In certain embodiments, the at least one CFTR allele comprises ΔF508 or the wild-type version thereof.

In some embodiments, the present invention provides kits and compositions comprising oligonucleotide detection assays configured for detecting a set of CFTR alleles, wherein the set is selected from: a) a first set comprising 2789+5G>A, R1162X, R560T, 1898+1G>A, delI507, I148T, and A455E; b) a second set comprising 3120+1G>A, 3659delC, G551D, N1303K, 1078delT, R334W, 711+1G>T, and 3849+10kb; c) a third set comprising 621+1G>T, W1282X, 1717-1G>A, and R117H; and d) fourth set comprising R347P, G85E, 2184delA, G542X, and R553X.

In other embodiments, the present invention provides kits and compositions comprising oligonucleotide detection assays configured for detecting a set of CFTR alleles, wherein the set is selected from: a) a first set comprising 2789+5G>A, R1162X, R560T, 1898+1G>A, delI507, I148T, and A455E; b) a second set comprising 3120+1G>A, 3659delC, G551D, N1303K, 1078delT, R334W, 711+1G>T, and 3849+10kb; c) a third set comprising 621+1G>T, W1282X, 1717-1G>A, and R117H; d) fourth set comprising R347P, G85E, G542X, and R553X, and e) a fifth set comprising 2184delA.

In certain embodiments, the oligonucleotide detection assays are selected from sequencing assays, polymerase chain reaction assays, hybridization assays, hybridization assays employing a probe complementary to a mutation, microarray assays, bead array assays, primer extension assays, enzyme mismatch cleavage assays, branched hybridization assays, rolling circle replication assays, NASBA assays, molecular beacon assays, cycling probe assays, ligase chain reaction assays, invasive cleavage structure assays, ARMS assays, and sandwich hybridization assays.

In some embodiments, the present invention provides methods of detecting an allele in the CFTR gene or method for diagnosing cystic fibrosis (or carrier status), comprising; a) providing; i) a sample from a subject; and ii) a composition comprising an oligonucleotide detection assay (e.g. as described herein); and b) contacting said sample with said composition such that the presence or absence of at least one allele in said CFTR gene is determined. In some embodiments, the sample is a blood sample, mouth swab sample, saliva sample, or other biological fluid sample from the subject.

Definitions

To facilitate an understanding of the present invention, a number of terms and phrases are defined below:

As used herein, the terms "subject" and "patient" refer to any organisms including plants, microorganisms and animals (e.g., mammals such as dogs, cats, livestock, and humans).

As used herein, the term "INVADER assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid.

In some embodiments, INVADER assay reagents are configured to detect a target nucleic acid sequence comprising first and second non-contiguous single-stranded regions separated by an intervening region comprising a double-stranded region. In preferred embodiments, the INVADER assay reagents comprise a bridging oligonucleotide capable of binding to said first and second non-contiguous single-stranded regions of a target nucleic acid sequence. In particularly preferred embodiments, either or both of said first or said second oligonucleotides of said INVADER assay reagents are bridging oligonucleotides.

In some embodiments, the INVADER assay reagents further comprise a solid support. For example, in some embodiments, the one or more oligonucleotides of the assay reagents (e.g., first and/or second oligonucleotide, whether bridging or non-bridging) is attached to said solid support.

In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components".

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In other embodiments, In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a sub-portion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include but are not limited to dyes; radiolabels such as $^{32}P$; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementarity between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modem biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr. Thermodynamics and NMR of internal G.T mismatches in DNA. Biochemistry 36, 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the Cleavase enzymes, the FEN-1 endonucleases (including RAD2 and XPG proteins), Taq DNA polymerase and *E. Coli* DNA polymerase I. The cleavage means may include enzymes having 5' nuclease activity (e.g., Taq DNA polymerase (DNAP), *E. Coli* DNA polymerase I). The cleavage means may also include modified DNA polymerases having 5' nuclease activity but lacking synthetic activity. Examples of cleavage means suitable for use in the method and kits of the present invention are provided in U.S. Pat. Nos. 5,614,402; 5,795,763; 5,843,669; 6,090; PCT Appln. Nos WO 98/23774; WO 02/070755A2; and WO0190337A2, each of which is herein incorporated by reference it its entirety.

The term "thermostable" when used in reference to an enzyme, such as a 5' nuclease, indicates that the enzyme is functional or active (i.e., can perform catalysis) at an elevated temperature, i.e., at about 55° C. or higher.

The term "cleavage products" as used herein, refers to products generated by the reaction of a cleavage means with a cleavage structure (i.e., the treatment of a cleavage structure with a cleavage means).

The term "target nucleic acid" refers to a nucleic acid molecule containing a sequence that has at least partial complementarity with at least a probe oligonucleotide and may also have at least partial complementarity with an INVADER oligonucleotide. The target nucleic acid may comprise single- or double-stranded DNA or RNA.

The term "non-target cleavage product" refers to a product of a cleavage reaction that is not derived from the target nucleic acid. As discussed above, in the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide" refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide—whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular polymorphism (e.g., SNP, repeat sequence, etc.) in a target sequence (e.g. genomic DNA) that has not been amplified (e.g. by PCR), without creating copies of the target sequence. A "non-amplified oligonucleotide detection assay" may, for example, amplify a signal used to indicate the presence or absence of a particular polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include comprise modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "multi-drug resistant" or multiple-drug resistant" refers to a microorganism which is resistant to more than one of the antibiotics or antimicrobial agents used in the treatment of said microorganism.

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (i.e., cleave) or elongate the oligonucleotide is encompassed within the term "reactant."

As used herein, the term "purified" or "to purify" refers to the removal of contaminants from a sample. For example, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n-1).

The term "nucleic acid sequence" as used herein refers to an oligonucleotide, nucleotide or polynucleotide, and fragments or portions thereof, and to DNA or RNA of genomic or synthetic origin which may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF THE DRAWINGS

FIG. 2 shows a table of invasive cleavage structure assay components (e.g., oligonucleotide INVADER assay components) for use in detecting the indicated mutations or genes. The INVADER assay components may be used as individual sets (e.g., the components used to detect a mutation at an individual locus) or may be grouped as they would be used together in a single pooled or multiplex reaction (See Exemplary Pool column). Examples of such combinations are also described below, e.g., in Example 1.

FIG. 3 provides an example of data generated using the procedure described in Example 1 in combination with the indicated oligonucleotide INVADER assay reagents, as described herein and as shown in FIG. 2.

DESCRIPTION OF THE INVENTION

Figure 1:
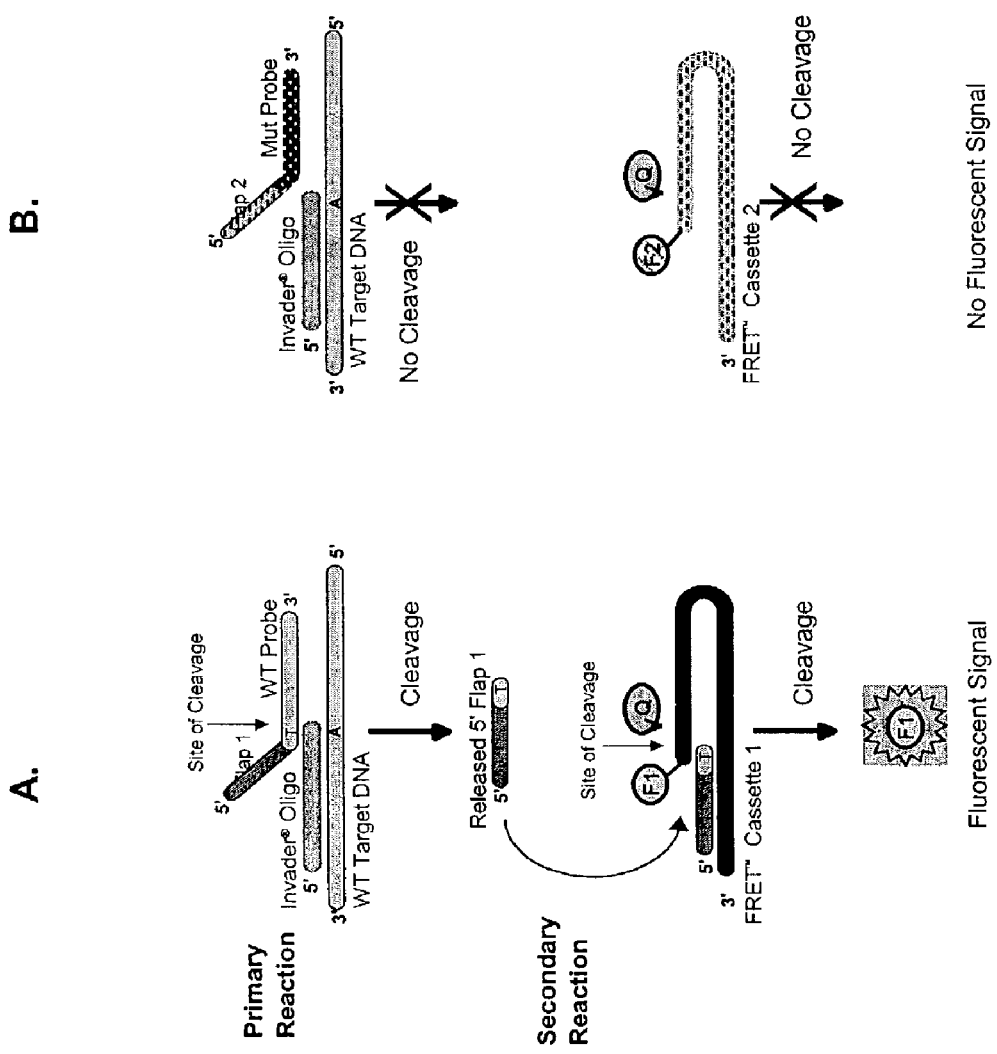
FIG. 1 shows a schematic diagram of INVADER oligonucleotides, probe oligonucleotides and FRET cassettes for detecting a two different alleles (e.g., differing by a single nucleotide) in a single reaction.

The present invention provides means for forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products are indicative of the presence of specific target nucleic acid sequences in the sample. When two strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, and 6,090,543, WO 97/27214 WO 98/42873, Lyamichev et al., Nat. Biotech., 17:292 (1999), Hall et al., PNAS, USA, 97:8272 (2000), each of which is herein incorporated by reference in their entirety for all purposes).

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 6,090,543; 5,994,069; Lyamichev et al., Nat. Biotech., 17:292 (1999), Hall et al., PNAS, USA, 97:8272 (2000), WO97/27214 and WO98/42873, each of which is herein incorporated by reference in their entirety for all purposes).

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific mutations and SNPs in unamplified, as well as amplified, RNA and DNA including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site designed oligonucleotides and/or bridging oligonucleotides. Such methods, procedures and compositions are described in U.S. Pat. No. 6,194,149, WO9850403, and WO0198537, all of which are specifically incorporated by reference in their entireties.

In certain embodiments, the target nucleic acid sequence is amplified prior to detection (e.g. such that synthetic nucleic acid is generated). In some embodiments, the target nucleic acid comprises genomic DNA. In other embodiments, the target nucleic acid comprises synthetic DNA or RNA. In some preferred embodiments, synthetic DNA within a sample is created using a purified polymerase. In some preferred embodiments, creation of synthetic DNA using a purified polymerase comprises the use of PCR. In other preferred embodiments, creation of synthetic DNA using a purified DNA polymerase, suitable for use with the methods of the present invention, comprises use of rolling circle amplification, (e.g., as in U.S. Pat. Nos. 6,210,884, 6,183,960 and 6,235,502, herein incorporated by reference in their entireties). In other preferred embodiments, creation of synthetic DNA comprises copying genomic DNA by priming from a plurality of sites on a genomic DNA sample. In some embodiments, priming from a plurality of sites on a genomic DNA sample comprises using short (e.g., fewer than about 8 nucleotides) oligonucleotide primers. In other embodiments, priming from a plurality of sites on a genomic DNA comprises extension of 3' ends in nicked, double-stranded genomic DNA (i.e., where a 3' hydroxyl group has been made available for extension by breakage or cleavage of one strand of a double stranded region of DNA). Some examples of making synthetic DNA using a purified polymerase on nicked genomic DNAs, suitable for use with the methods and compositions of the present invention, are provided in U.S. Pat. No. 6,117,634, issued Sep. 12, 2000, and U.S. Pat. No. 6,197,557, issued Mar. 6, 2001, and in PCT application WO 98/39485, each incorporated by reference herein in their entireties for all purposes.

In some embodiments, the present invention provides methods for detecting a target sequence, comprising: providing a) a sample containing DNA amplified by extension of 3' ends in nicked double-stranded genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In other embodiments, synthetic DNA suitable for use with the methods and compositions of the present invention is made using a purified polymerase on multiply-primed genomic DNA, as provided, e.g., in U.S. Pat. Nos. 6,291,187, and 6,323,009, and in PCT applications WO 01/88190 and WO 02/00934, each herein incorporated by reference in their entireties for all purposes. In these embodiments, amplification of DNA such as genomic DNA is accomplished using a DNA polymerase, such as the highly processive Φ29 polymerase (as described, e.g., in U.S. Pat. Nos. 5,198,543 and 5,001,050, each herein incorporated by reference in their entireties for all purposes) in combination with exonuclease-resistant random primers, such as hexamers.

In some embodiments, the present invention provides methods for detecting a target sequence, comprising: providing a) a sample containing DNA amplified by extension of multiple primers on genomic DNA, said genomic DNA suspected of containing said target sequence; b) oligonucleotides capable of forming an invasive cleavage structure in the presence of said target sequence; and c) exposing the sample to the oligonucleotides and the agent. In some embodiments, the agent comprises a cleavage agent. In some preferred embodiments, said primers are random primers. In particularly preferred embodiments, said primers are exonuclease resistant. In some particularly preferred embodiments, the method of the invention further comprises the step of detecting said cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, said wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In certain embodiments, the present invention provides kits for assaying a pooled sample (e.g., a pooled blood sample) using INVADER detection reagents (e.g. primary probe, INVADER probe, and FRET cassette). In preferred embodiments, the kit further comprises instructions on how to perform the INVADER assay and specifically how to apply the INVADER detection assay to pooled samples from many individuals, or to "pooled" samples from many cells (e.g. from a biopsy sample) from a single subject.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, [The kinetics of oligonucleotide replacement. Luis P. Reynaldo, Alexander V. Vologodskii, Bruce P. Neri and Victor I. Lyamichev. J. Mol. Biol. 97: 511-520 (2000)], multiple probes can hybridize to the same target, allowing multiple cleavages, and the generation of multiple cleavage products.

The INVADER Assay Reaction:

In the INVADER DNA Assay, two oligonucleotides (a discriminatory Primary Probe and an INVADER Oligo) hybridize in tandem to the target DNA to form an overlapping structure. The 5'-end of the Primary Probe includes a 5'-flap that does not hybridize to the target DNA (FIG. 1). The 3'-nucleotide of the bound INVADER Oligo overlaps the Primary Probe, but need not hybridize to the target DNA. The CLEAVASE enzyme recognizes this overlapping structure and cleaves off the unpaired 5'-flap of the Primary Probe, releasing it as a target-specific product. The Primary Probe is designed to have a melting temperature close to the reaction temperature. Thus, under the isothermal assay conditions, Primary Probes, which are provided in excess, cycle on the target DNA. This allows for multiple rounds of Primary Probe cleavage for each target DNA, and amplification of the number of released 5'-flaps.

In the secondary reaction, each released 5'-flap can serve as an INVADER oligonucleotide on a fluorescence resonance energy transfer (FRET) Cassette to create another overlapping structure that is recognized and cleaved by the CLEAVASE enzyme (FIG. 1). When the FRET Cassette is cleaved, the fluorophore (F) and quencher (Q) are separated, generating detectable fluorescence signal. Similar to the initial reaction, the released 5'-flap and the FRET Cassette cycle, resulting in amplified fluorescence signal. The initial and secondary reactions run concurrently in the same well.

The biplex format of the INVADER DNA assay enables simultaneous detection of two DNA sequences in a single well. Most often, this involves detection of two variants of a particular polymorphism. The biplex format uses two different discriminatory Primary Probes, each with a unique 5'-flap, and two different FRET Cassettes, each with a spectrally distinct fluorophore. By design, the released 5'-flaps will bind only to their respective FRET Cassettes to generate a target-specific signal.

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). By way of example, and not intending to limit the kits of the present invention to any particular configuration or combination of components, the following section describes one embodiment of a kit for practicing the present invention:

In some embodiments, the kits of the present invention provide the following reagents:

| CLEAVASE enzyme (e.g., CLEAVASE X) | Primary Oligos |
|---|---|
| DNA Reaction Buffer 1 | INVADER Oligo |
| | FRET Cassette 1 (e.g., F) |
| | FRET Cassette 2 (e.g., R) |
| | Mutant DNA controls |
| | Wild type DNA controls |
| | "No Target" Blank control |

In some embodiments, the kits of the present invention provide the following reagents:

| CLEAVASE enzyme mix (e.g., CLEAVASE X) in 140 mM MgCl$_2$, 24% glycerol | Mutation Mixes containing the following constituents in 25 mM MOPS, pH 7.5: Primary Oligos INVADER Oligos FRET Cassette 1 (e.g., F) FRET Cassette 2 (e.g., a second F cassette) |
|---|---|

-continued

FRET Cassette 3 (e.g. R)
Mutant DNA controls
Internal DNA controls
"No Target" Blank control Examples of Primary Oligonucleotides and Secondary Oligonucleotides suitable for use with the methods of the present invention are provided in FIG. 2. While the oligonucleotides shown therein may find use in a number of the methods, and variations of the methods, of the present invention, these INVADER assay oligonucleotide sets find particular use with kits of the present invention. The oligonucleotide sets shown in FIG. 2 may be used as individual sets to detect individual target DNAs, or may be combined in biplex or multiplex reactions for the detection of two or more analytes or controls in a single reaction.

In preferred embodiments, the oligonucleotides shown in FIG. 2 (or similar oligonucleotides) are used in invasive cleavage structure assays (e.g. INVADER assays) to detect alleles in the CFTR gene. In preferred embodiments, pools or sets of the assay configurations shown in FIG. 2 are used to simultaneously detect a plurality of CFTR alleles (e.g. 1-8 CFTR alleles are detected simultaneously in a single reaction container). In this regard, for example, the approximately 25 different alleles shown in FIG. 2 could be split into 4-5 pools (as shown) which would only require 4-5 different reaction vessels to detect all of the CFTR alleles shown. In other embodiments, the 25 different alleles shown in FIG. 2 are split into 5 pools, plus separate SNP detection for ΔF508 which would only require 6 different reaction vessels to detect all of the CFTR alleles shown.

Certain design considerations can be used to design pools or sets of CFTR alleles to detect by invasive cleavage structure assays. One consideration that may be used is to avoid physical overlap of oligonucleotides designed to detect closely spaced mutations (this is satisfied by the exemplary pools shown in FIG. 2). Another consideration has to do with the signal generation capabilities of the individual invasive cleavage structure assays. For example, often the signal generated from a particular INVADER oligonucleotide and probe pair is higher or lower than that generated from another pair assayed under the same reaction conditions. While in some cases it is feasible and/or desirable to alter oligonucleotide design to modulate such differences in signal generation capabilities, in other cases it may not possible or worthwhile to do so. As such, CFTR mutations can be pooled based on variability in signal generation that dictates that certain pairs be grouped together such that relatively weak signal generating pairs are not overwhelmed by relatively strong signal generating pairs.

An additional consideration has to do with undesired effects resulting from particular combinations of oligonucleotides in a single reaction. One such effect is target-independent generation of background signal. Certain oligonucleotides in combination with others may generate signal in the INVADER assay in the absence of the particular target being detected. Separation of these oligonucleotide combinations into different pools can be used to alleviate this effect. Similarly, certain oligonucleotide combinations can artificially repress signal generation from a desired target. Again, separation of these combinations into different pools can alleviate this effect.

It is contemplated that the designs of these probes sets (e.g., the oligonucleotides and/or their sequences) may be adapted for use in RNA detection assays, using the guidelines for reaction design and optimization provided herein. In some embodiments, a kit of the present invention provides a list of additional components (e.g., reagents, supplies, and/or equipment) to be supplied by a user in order to perform the methods of the invention. For example, and without intending to limit such additional components lists to any particular components, one embodiment of such a list comprises the following:

Clear CHILLOUT-14 liquid wax (MJ Research) or RNase-free, optical grade mineral oil (Sigma, Cat. No. M-5904)
96-well polypropylene microplate (MJ Research, Cat. No. MSP-9601)
Sterile 1.5-ml or 2.0-ml microcentrifuge tubes
Sterile, DNase/RNase free disposable aerosol barrier pipet tips
Multichannel pipets (0.5-10 μl, 2.5-20 μl)
Thermal cycler or other heat source (e.g., lab oven or heating block).
Miscellaneous laboratory equipment (tube racks, micropipetors, multichannel pipet, microcentrifuge, vortex mixer).
Fluorescence microplate reader (a preferred plate reader is top-reading, equipped with light filters have the following characteristics:

| Excitation (Wavelength/Bandwidth) | Emission (Wavelength/Bandwidth) |
| --- | --- |
| 485 nm/20 nm | 530 nm/25 nm |
| 560 nm/20 nm | 620 nm/40 nm |

In some embodiments, a kit of the present invention provides a list of optional components (e.g., reagents, supplies, and/or equipment) to be supplied by a user to facilitate performance of the methods of the invention. For example, and without intending to limit such optional components lists to any particular components, one embodiment of such a list comprises the following:

Sterile 8-tube strip or microplate (optional)
Disposable plastic trough (optional)
Plate sealing tape (optional)

In some embodiments, a kit of the present invention provides a list of required components to be supplied by a user to facilitate performance of the methods of the invention for which multiple alternatives are acceptable (e.g. sample preparation kits). For example, and without intending to limit such optional components lists to any particular components, one embodiment of such a list comprises the following:

QIAGEN QIAamp® Blood Kit
Gentra Systems PUREGENE™ Kit
Gentra Systems GENERATION® Products In some embodiments of a kit, detailed protocols are provided. In preferred embodiments, protocols for the assembly of INVADER assay reactions (e.g., formulations and preferred procedures for making reaction mixtures) are provided. In particularly preferred embodiments, protocols for assembly of reaction mixtures include computational or graphical aids to reduce risk of error in the performance of the methods of the present invention (e.g., tables to facilitate calculation of volumes of reagents needed for multiple reactions, and plate-layout guides to assist in configuring multi-well assay plates to contain numerous assay reactions). By way of example, and without intending to limit such protocols to any particular content or format, kits of the present invention may comprise the following protocol:

I. Detailed DNA Biplex INVADER Assay Protocol
1. Determine the number of samples and controls to be tested.
2. Plan the microplate layout for each experimental run (e.g., samples, controls). Inclusion of a No Target Control (tRNA Carrier in buffered, nuclease-free water) is required for a valid result.
3. Prepare the INVADER DNA Assay Reaction Mix for the biplex assay format. To calculate the volumes of reaction components needed for the assay (X Volume), multiply the total number of reactions (samples and controls) by 1.25 [X Volume (μl)=# reactions×1.25]. Vortex the INVADER DNA Assay Reaction Mix briefly after the last reagent addition to mix thoroughly.

INVADER DNA Assay Reaction Mix
Biplex Assay Format

| Reaction Components | 1X Volume | __X Volume |
|---|---|---|
| DNA Reaction Buffer 1 | 5.0 μl | |
| FRET F Cassette | 1.0 μl | |
| FRET R Cassette | 1.0 μl | |
| Primary Probes | 1.0 μl | |
| INVADER Oligo | 1.0 μl | |
| CLEAVASE enzyme | 1.0 μl | |
| Total Mix Volume (1×) | 10.0 μl | |

4. Add 10 μl of each control or DNA sample (≧150 ng DNA) to the appropriate well and mix by pipetting up and down 1-2 times. Overlay each reaction with 20 μl of clear CHILLOUT or mineral oil. Seal microplate with Thermaseal well tape (optional).
5. Incubate reactions for 5 minutes at 95° C. in a thermal cycler or oven.
6. Lower the temperature to 63° C. in the thermal cycler or transfer the plate to a 63° C. heat block, then add 10 μl of the INVADER® DNA Assay Reaction Mix to each well and mix well by pipetting up and down 3 to 5 times. An 8-tube strip or microplate may be used to facilitate addition of the INVADER® DNA Assay Reaction Mix using a multichannel pipet. When adding the INVADER® DNA Assay Reaction Mix, be sure to add the mix below the level of the mineral oil or Chill-out™ 14 liquid wax.
7. Cover the microplate with plate sealing tape (optional) and incubate at 63° C. for 4 hours.
8. After the 4-hour incubation, place the microplate in the plate holder of the fluorescence plate reader. Remove plate sealing tape, if used.
9. Read the plate at the two different wavelength settings (The dye corresponding to the WT and Mut signal is not necessarily the same for all biplex assays).
10. The gain should be set so that Control 4 reads between 100 and 200 for each scan. The Control 4 values do not have to be identical for the F and R dye scans.
    NOTE: Remove the microplate seal before reading the microplate.

This procedure enables collection of multiple data sets to extend the assay's dynamic range. During the secondary INVADER reaction, read the microplate directly in a top-reading fluorescence microplate reader.
   NOTE: Because the optimal gain setting can vary between instruments, adjust the gain as needed to give the best signal/background ratio (sample raw signal divided by the No Target Control signal) or No Target Control sample readings of ~100 RFUs. Fluorescence microplate readers that use a xenon lamp source generally produce higher RFUs. For directly reading the microplates, the probe height of, and how the plate is positioned in, the fluorescence microplate reader may need to be adjusted according to the manufacturer's recommendations.

In another embodiment, such kits and methods may comprise the following protocol.

Pool Assay Protocol
1. Make up the INVADER DNA reaction mixes according to the following recipe.

| | | ΔF508 | Pool |
|---|---|---|---|
| Number of Samples | 4 | | |
| Number of Reactions | | 8 | 7 |
| Add 25% | | 2 | 1.75 |
| Number of Reactions for Mix Calculations | | 10 | 8.75 |

| Component | Lot # | Amount Per Reaction (μl) | Volume to Add (μl) | Component Added (Check off after adding) |
|---|---|---|---|---|
| CFTR (ΔF508) Reaction Mixes | | | | |
| INVADER Assay Reaction Mix | | | | |
| CFTR (ΔF508) INVADER Oligo (I) | | 2 | 20 | |
| CFTR (ΔF508) Primary Probes (P) | | 2 | 20 | |
| CFTR (ΔF508) FRETs (F) | | 4 | 40 | |
| Enzyme Mix (EM)) | | 2 | 20 | |
| Total Volume | | 10 | 100 | |
| CFTR (Mutation Pool 1) Reaction Mixes | | | | |
| INVADER Assay Reaction Mix | | | | |
| CFTR Mix 1 (M1) | | 8 | 70 | |
| Enzyme Mix (EM)) | | 2 | 18 | |
| Total Volume | | 10 | 88 | |
| CFTR (Mutation Pool 2) Reaction Mixes | | | | |
| INVADER Assay Reaction Mix | | | | |
| CFTR Mix 2 (M2) | | 8 | 70 | |
| Enzyme Mix (EM) | | 2 | 18 | |
| Total Volume | | 10 | 88 | |
| CFTR (Mutation Pool 3) Reaction Mixes | | | | |
| INVADER Assay Reaction Mix | | | | |
| CFTR Mix 3 (M3) | | 8 | 70 | |
| Enzyme Mix (EM)) | | 2 | 18 | |
| Total Volume | | 10 | 88 | |
| CFTR (Mutation Pool 4) Reaction Mixes | | | | |

INVADER Assay

-continued

| Reaction Mix | | |
|---|---|---|
| CFTR Mix 4 (M4) | 8 | 70 |
| Enzyme Mix (EM) | 2 | 18 |
| Total Volume | 10 | 88 |

2. Following the sample layout, aliquot 10 μl of controls and samples (≧150 ng DNA) into a 96-well low profile microplate.
3. To prevent evaporation, overlay each well with 20 μl of clear Chill-out™ or mineral oil using a multichannel pipet.
4. Aliquot the 5 reaction mixes into 5 wells of an 8-well strip in the following order:
   well 1: ΔF508 mix
   well 2: Pool 1 mix
   well 3: Pool 2 mix
   well 4: Pool 3 mix
   well 5: Pool 4 mix
5. Incubate samples at 95° C. for 5 minutes in a thermal cycler.
6. Lower the temperature of the thermal cycler to 63° C., then add 10 μl of the appropriate INVADER® DNA Assay Reaction Mix to each well and mix by pipetting up and down 3-5 times. For this addition, use 5 consecutive tips of an 8 channel pipette, and aliquot reaction mix into each well moving down the plate, starting with row A, column 1. Remember to change pipet tips after each Reaction Mix addition. If running more than 4 patients, start again at row A, column 6. See Appendix D for full plate layout. Add the mix below the level of the Chill-out™ or mineral oil.
7. Incubate the reactions at 63° C. for 5 hours.
8. After the 5 hour incubation place the low profile microplate in a plate holder in the fluorescence plate reader and read using the following parameters:

| | CytoFluor® | | GENios™ | |
|---|---|---|---|---|
| | FAM | Red | FAM | Red |
| Excitation: | 485 nm/20 nm | 560 nm/20 nm | 485 nm/20 nm | 560 nm/20 nm |
| Emission: | 530 nm/25 nm | 620 nm/40 nm | 535 nm/25 nm | 612 nm/10 nm |

Adjust the gain setting for each scan to give No Target Blank values between 100 and 200 AFU's.
9. Analyze results according to guidelines for using the ratios of the two fluorescent signals.

In a preferred embodiment, the pool assay format comprises an additional pool such that there are five mutation pool reaction mixes. In this case, the fifth pool is treated as described for pools 1-4 throughout the entire procedure described above, such that detection of all mutations can be accomplished in a total of 6 reaction wells.

Calculation of Ratios and Guidelines for Interpretation

In some embodiments of a kit, guidelines for using the ratios of the two fluorescent signals to determine a genotype are provided. For example, for each allele of a given polymorphism, the net signal/background, or Net Fold Over Zero (FOZ−1), values may be calculated as follows for the signal obtained with each dye:

$$FOZ = \frac{\text{Raw counts from sample}}{\text{Raw counts from No Target Blank}}$$

The two FOZ values (i.e. wild type and mutant) for each sample were used to calculate the WT:Mut Ratio as follows:

$$\text{Ratio} = \frac{\text{(Net WT } FOZ\text{)}}{\text{(Net Mut } FOZ\text{)}}$$

where Net FOZ=FOZ−1

In some embodiments, supplementary documentation, such as protocols for ancillary procedures, e.g., for the preparation of additional reagents, or for preparation of samples for use in the methods of the present invention, are provided. In preferred embodiments, supplementary documentation includes guidelines and lists of precautions provided to facilitate successful use of the methods and kits by unskilled or inexperienced users. In particularly preferred embodiments, supplementary documentation includes a troubleshooting guide, e.g., a guide describing possible problems that may be encountered by users, and providing suggested solutions or corrections to intended to aid the user in resolving or avoiding such problems.

For example, and without intending to limit such supplementary documentation to any particular content, kits of the present invention may comprise any of the following procedures and guidelines:

II. Sample Preparation

In preferred embodiments, samples are diluted to concentrations that correspond to a 10-μl addition per reaction. The concentration of a 100-ng sample should be 15 ng/μl.

The assay is optimized for performance with genomic DNA samples prepared from whole blood or buffy coat. Several DNA extraction methods/kits have been validated for performance in the Biplex INVADER assay:
   QIAGEN QIAamp® Blood Kit
   Gentra Systems PUREGENE™ Kit
   Gentra Systems GENERATION® Products Quantitation is not necessary if using one of these recommended sample preparation methods (i.e., QIAGEN or Gentra). In other embodiments, the DNA sample should be quantitated. In a preferred embodiment, such quantitation is accomplished using the PicoGreen® or OliGreen® assay. Quantitating by $A_{260}/A_{280}$ can lead to an overestimation of the amount of DNA in the sample due to RNA contamination. A low $A_{260}/A_{280}$ reading (<1.5) indicates there is an overabundance of protein in the sample. In particularly preferred embodiments, only samples with a concentration >10 ng/μl are used in the INVADER DNA Assay.

| Problem | Possible Solution |
|---|---|
| No Signal or Low Signal | Assay: Mixing inconsistencies. Make sure all reagents are properly mixed prior to assembly of INVADER ® DNA Assay Reaction Mix. The controls and INVADER ® DNA Assay Reaction Mixes must be mixed thoroughly and consis- |

| Problem | Possible Solution |
|---|---|
| | tently before the plate is set up. During addition of INVADER ® DNA Assay Reaction Mix to sample plate, mix by pipetting up and down several times, ensuring that all liquid is expelled before removing the tip. Verify that reagents were added in the correct sequence, to the correct mix, and that the correct mix is added to the appropriate controls/sample wells (refer to sample plate layout). Verify that all reagents were stored at the proper temperature as indicated in this package insert. Make sure that 10 μl of the appropriate control was added to each well. Make sure that the 10 μl of the appropriate INVADER ® DNA Assay Reaction Mix was added below the level of the mineral oil or Chill-out ™ 14 liquid wax. Not adding the correct amount will result in loss of signal. Verify that the correct INVADER ® DNA Assay Reaction Mix is added to the appropriate control. Make sure assay is run for at five hours at 63° C. Use mineral oil or clear Chill-out ™ 14 liquid wax to prevent evaporation during the reaction. Instrument: Verify that the fluorescence plate reader is set to the correct excitation and emission wavelengths for each scan. If possible, run a diagnostic test on the fluorescence plate reader to ensure that the instrument and light source are working properly. Verify that two scans were performed at two different wavelengths. Make sure the proper "96-well plate type" has been selected in the fluorescence plate reader. Verify that the coordinates of the plate are programmed correctly in the fluorescence plate reader. Signal should be read in the middle of the well and at an optimal distance from the plate for best results. Incubations should be conducted in properly calibrated heating units. Checking these units on a regular basis using a thermocouple thermometer equipped with a probe traceable to NIST standards is recommended. Make sure that the plate is firmly seated in the thermal cycler or heat block. |
| High Signal in Control 4 (No Target Blank) | Assay: Use DNase/RNase free aerosol barrier tips and sterile tubes for making the INVADER ® DNA Assay Reaction Mix. Make sure that pipet tips are changed after each use. Wear gloves when setting up the assay. Make sure that pipet tips do not touch any other surfaces except the solution being pipetted, since nucleases may be present. Do not touch pipet tips with hands. Instrument: Adjust the gain setting of the fluorescence plate reader such that Control 4 (No Target Blank) reads approximately 200 for each scan. |
| Fluorescent Signal Is Off-scale | Assay: Use DNase/RNase free aerosol barrier tips and sterile tubes for making the INVADER ® DNA Assay Reaction Mix. Confirm that the incubations were done for the correct amount of time and at the correct temperature. Instrument: Adjust the gain of the fluorescence |

| Problem | Possible Solution |
|---|---|
| | plate reader. The gain of the two scans should be set so that Control 4 (No Target Blank) reads at least 100 for each scan; however, an approximate level of 200 is recommended. Allow the lamp in the fluorescence plate reader to warm up for at least 10 minutes before reading the results. |

EXAMPLES

Example 1

Reagents and Methods for Detection of Cystic Fibrosis Transmembrane Conductance Regulator (CFTR) Mutations The following examples serve to illustrate certain preferred embodiments and aspects of the present invention and are not to be construed as limiting the scope thereof. Ex. (Example); Fig. (Figure); ° C. (degrees Centigrade); g (gravitational field); hr (hour); min (minute); olio (oligonucleotide); rxn (reaction); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); p (plasmid); μl (microliters); ml (milliliters); μg (micrograms); mg (milligrams); M (molar); mM (milliMolar); μM (microMolar); pmoles (picomoles); amoles (attomoles); zmoles (zeptomoles); nm (nanometers); kdal (kilodaltons); OD (optical density); EDTA (ethylene diamine tetra-acetic acid); FITC (fluorescein isothiocyanate); SDS (sodium dodecyl sulfate); $NaPO_4$ (sodium phosphate); NP-40 (Nonidet P-40); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA); PBS (phosphate buffered saline); PPBS (phosphate buffered saline containing 1 mM PMSF); PAGE (polyacrylamide gel electrophoresis); Tween (polyoxyethylene-sorbitan); Red (REDMOND RED Dye, Epoch Biosciences, Bothell Wash.) Z28 (ECLIPSE Quencher, Epoch Biosciences, Bothell, Wash.); ATCC (American Type Culture Collection, Rockville, Md.); Coriell (Coriell Cell Repositories, Camden, N.J.); DSMZ (Deutsche Sammlung von Mikroorganismen und Zellculturen, Braunschweig, Germany); Ambion (Ambion, Inc., Austin, Tex.); Boehringer (Boehringer Mannheim Biochemical, Indianapolis, Ind.); MJ Research (MJ Research, Watertown, Mass.; Sigma (Sigma Chemical Company, St. Louis, Mo.); Dynal (Dynal A.S., Oslo, Norway); Gull (Gull Laboratories, Salt Lake City, Utah); Epicentre (Epicentre Technologies, Madison, Wis.); Lampire (Biological Labs., Inc., Coopersberg, Pa.); MJ Research (MJ Research, Watertown, Mass.); National Biosciences (National Biosciences, Plymouth, Minn.); NEB (New England Biolabs, Beverly, Mass.); Novagen (Novagen, Inc., Madison, Wis.); Perkin Elmer (Perkin-Elmer/ABI, Norwalk, Conn.); Promega (Promega, Corp., Madison, Wis.); Stratagene (Stratagene Cloning Systems, La Jolla, Calif.); Clonetech (Clonetech, Palo Alto, Calif.) Pharmacia (Pharmacia, Piscataway, N.J.); Milton Roy (Milton Roy, Rochester, N.Y.); Amersham (Amersham International, Chicago, Ill.); and USB (U.S. Biochemical, Cleveland, Ohio). Glen Research (Glen Research, Sterling, Va.); Coriell (Coriell Cell Repositories, Camden, N.J.); Gentra (Gentra, Minneapolis, Minn.); Third Wave Technologies (Third Wave Technologies, Madison, Wis.); PerSeptive Biosystems (PerSeptive Biosystems, Framington, Mass.); Microsoft (Microsoft, Redmond, Wash.); Qiagen (Qiagen, Valencia, Calif.); Molecular Probes (Molecular Probes, Eugene, Oreg.); VWR (VWR Scientific); Advanced Biotechnologies (Advanced Biotechnologies, INC., Columbia, Md.).

Reagents:
CFTR (2184delA) Control (1 vial marked "2184delA", 250 µl)
CFTR (1898+1G>A) Control (1 vial marked "1898+1G>A", 250 µl)
CFTR (I148T) Control (1 vial marked "1148T", 250 µl)
CFTR (1078delT) Control (1 vial marked "1078delT", 250 µl)
CFTR (W1282X) Control (1 vial marked "W1282X", 250 µl)
CFTR (621+1G>T) Control (1 vial marked "621+1G>T", 250 µl)
Control 4 (No Target Blank) (1 vial marked "C4", 1250 µl)
Cleavase® X/CF Enzyme or Cleavase Enzyme Mix (20 ng/µl, 1 vial, 1250 µl)

Reagent Composition:
CFTR (2184delA) Control is a plasmid construct containing the 2184delA sequence suspended in yeast tRNA and buffered nuclease-free water. CFTR (1898+1G>A) Control, CFTR (1148T) Control, CFTR (1078delT) Control, CFTR (W1282X) and CFTR (621+1G>T) Control are synthetic oligonucleotides suspended in yeast tRNA and buffered nuclease-free water. Control 4 (No Target Blank) contains yeast tRNA in buffered nuclease-free water.

Control Usage:
1. Determine the number (singlicate, duplicate, triplicate, quadruplicate) of controls to be tested. Use 10 µl of control material in each reaction.
2. Treat control materials the same as test samples throughout the INVADER® DNA Assay.
3. Control materials and test samples should be analyzed on a fluorescence plate reader.

Expected Results:
CFTR (2184delA) Control and CFTR (1898+1G>A) Control material should react with only the CFTR Mix 1 (F dye signal); CFTR (I148T) Control and CFTR (1078delT) material should react with only the CFTR Mix 2 (F dye signal); CFTR (W1282X) Control material should react with only the CFTR Mix 3 (F dye signal); CFTR (621+1G>T) Control should react with only the CFTR Mix 4 (F dye signal); and Control 4 (No Target Blank) material should show only R dye signal but not F dye signal with any of the CFTR Mixes 1-4 (F dye and R dye signals). Actual signal values depend on reaction volumes, test methods, and the fluorescence plate reader used.

Preparation of INVADER DNA Reaction Mixes 1-4 (mixes were scaled by number of reactions times 1.25):

| Component (mixed prior to addition) | Volume (per rxn) to Reaction Mix 1 | Volume (per rxn) to Reaction Mix 2 | Volume (per rxn) to Reaction Mix 3 | Volume (per rxn) to Reaction Mix 4 |
|---|---|---|---|---|
| CFTR Mix 1 | 8 µl | 0 | 0 | 0 |
| CFTR Mix 2 | 0 | 8 µl | 0 | 0 |
| CFTR Mix 3 | 0 | 0 | 8 µl | 0 |
| CFTR Mix 4 | 0 | 0 | 0 | 8 µl |
| Cleavase enzyme mix | 2 µl | 2 µl | 2 µl | 2 µl |
| Total | 10 µl | 10 µl | 10 µl | 10 µl |

2. 10 µl of each target DNA (sample or control) was aliquoted into an assigned reaction well.
3. 20 µl of Mineral Oil was added to each well to prevent evaporation.
4. Samples were incubated at 95° C. for 5 minutes in a thermal cycler.
5. After the temperature was reduced to 63° C.; 10 µl of the INVADER® DNA Assay Reaction Mixes were added to the appropriate wells, taking care to add the reaction mix below the mineral oil.
6. Reactions were incubated at 63° C. for 5 hours in a thermal cycler.
7. The reaction plate was read using the following settings on a CytoFluor® Series 4000 Fluorescence Multi-Well Plate Reader:

| Cycle 1 | Cycle 2 |
|---|---|
| Excitation = 485/20 | Excitation = 560/20 |
| Emission = 530/25 | Emission = 620/40 |
| Gain = 40 | Gain = 46 |
| Reads/well = 10 | Reads/well = 10 |

8. QA acceptance criteria for positive and negative samples:

TABLE 1

Mix 1 criteria. Ratio = FAM AdjNetFOZ (0.01 if <= 0/RedFOZ-1)

| Ratio | FamFOZ | RedFOZ | Genotype |
|---|---|---|---|
| >0.4 | >1.75 | >=2.0 | Positive |
| >0.4 | <=1.75 | >=2.0 | Low signal |
| <0.275 | NA | >=2.0 | Negative |
| >=0.275 and <=0.4 | NA | >=2.0 | EQ |
| NA | NA | <2.0 | Low signal |

TABLE 2

Mix 2 criteria.

| Ratio | FamFOZ | RedFOZ | Genotype |
|---|---|---|---|
| >0.25 | >1.75 | >=2.0 | Positive |
| >0.25 | <=1.75 | >=2.0 | Low signal |
| <0.175 | NA | >=2.0 | Negative |
| >=0.175 and <=0.25 | NA | >=2.0 | EQ |
| NA | NA | <2.0 | Low signal |

Ratio = FAM AdjNetFOZ (0.01 if <=0/RedFOZ-1)

TABLE 3

Mix 3 criteria.

| Ratio | FamFOZ | RedFOZ | Genotype |
|---|---|---|---|
| >0.3 | >1.75 | >=2.0 | Positive |
| >0.3 | <=1.75 | >=2.0 | Low signal |
| <0.2 | NA | >=2.0 | Negative |
| >=0.2 and <=0.3 | NA | >=2.0 | EQ |
| NA | NA | <2.0 | Low signal |

Ratio = FAM AdjNetFOZ (0.01 if <=0/RedFOZ-1

TABLE 4

Mix 4 criteria.

| Ratio | FamFOZ | RedFOZ | Genotype |
|---|---|---|---|
| >0.275 | >1.75 | >=2.25 | Positive |
| >0.275 | <=1.75 | >=2.25 | Low signal |
| <0.175 | NA | >=2.25 | Negative |
| >=0.175 and <=0.275 | NA | >=2.25 | EQ |
| NA | NA | <2.25 | Low signal |

Ratio = FAM AdjNetFOZ (0.01 if <=0/RedFOZ-1

Example 2

Alternative Oligonucleotide and Pool Configurations

In another embodiment, alternative designs were created for some of the oligonucleotides, and some oligonucleotides were included in different pools. These alternative reaction mixes were applied to the analysis of samples as described in Example 1.

Reagents:
CFTR (I148T) M1 Mut Control (1 vial marked "CA", 250 µl)
CFTR (1898+1G>A) M1 Mut Control (1 vial marked "CB", 250 µl)
CFTR (1078delT) M2 Mut Control (1 vial marked "CC", 250 µl)
CFTR (621+1G>T) M3 Mut Control (1 vial marked "CD", 250 µl)
CFTR (G542X) M4 Mut Control (1 vial marked "CE", 250 µl)
CFTR (2184delA) M5 Mut Control (1 vial marked "CF", 250 µl)
Control 4 (No Target Blank) (1 vial marked "C4", 1250 µl)
Cleavase® X/CF Enzyme or Cleavase Enzyme Mix (20 ng/µl, 1 vial, 1250 µl)

Reagent Composition:

CFTR (2184delA) M5 Mut Control is a plasmid construct containing the 2184delA sequence suspended in yeast tRNA and buffered nuclease-free water. CFTR (I148T) M1 Mut Control, CFTR (1898+1G>A) M1 Mut Control, CFTR (1078delT) M2 Mut Control, CFTR (621+1G>T) M3 Mut Control, and CFTR (G542X) M4 Mut Control are synthetic oligonucleotides suspended in yeast tRNA and buffered nuclease-free water. Control 4 (No Target Blank) contains yeast tRNA in buffered nuclease-free water.

Control Usage:
1. Determine the number (singlicate, duplicate, triplicate, quadruplicate) of controls to be tested. Use 10 µl of control material in each reaction.
2. Treat control materials the same as test samples throughout the INVADER® DNA Assay.
3. Control materials and test samples should be analyzed on a fluorescence plate reader.

Expected Results:

The CFTR (I148T) Control should react only with assays designed to detect the presence of the CFTR (I148T) mutant allele. The CFTR (1898+1G>A) Control should react only with assays designed to detect the presence of the CFTR (1898+1G>A) mutant allele. The CFTR (1078delT) Control should react only with assays designed to detect the presence of the CFTR (1078delT) mutant allele. The CFTR (621+1G>T) Control should react only with assays designed to detect the presence of the CFTR (621+1G>T) mutant allele. The CFTR (G542X) Control should react only with assays designed to detect the presence of the CFTR (G542X) mutant allele. The CFTR (2184delA) Control should react only with assays designed to detect the presence of the CFTR (2184delA) mutant allele. Control 4 (No Target Blank) does not contain any CFTR sequence and, therefore, should not react with any assay designed to detect the presence of a CFTR allele.

1. Preparation of INVADER DNA Reaction Mixes 1-4 (mixes were scaled by number of reactions times 1.25):

| Component (mixed prior to addition) | Volume (per rxn) to Reaction Mix 1 | Volume (per rxn) to Reaction Mix 2 | Volume (per rxn) to Reaction Mix 3 | Volume (per rxn) to Reaction Mix 4 | Volume (per rxn) to Reaction Mix 5 |
|---|---|---|---|---|---|
| CFTR Mix 1 | 8 µl | 0 | 0 | 0 | 0 |
| CFTR Mix 2 | 0 | 8 µl | 0 | 0 | 0 |
| CFTR Mix 3 | 0 | 0 | 8 µl | 0 | 0 |
| CFTR Mix 4 | 0 | 0 | 0 | 8 µl | 0 |
| CFTR Mix 5 | 0 | 0 | 0 | 0 | 8 µl |
| Cleavase enzyme mix | 2 µl | 2 µl | 2 µl | 2 µl | 2 µl |
| Total | 10 µl | 10 µl | 10 µl | 10 µl | 10 µl |

2. 10 µl of each target DNA (sample or control) was aliquoted into an assigned reaction well.
3. 20 µl of Mineral Oil was added to each well to prevent evaporation.
4. Samples were incubated at 95° C. for 5 minutes in a thermal cycler.
5. After the temperature was reduced to 63° C.; 10 µl of the INVADERS DNA Assay Reaction Mixes were added to the appropriate wells, taking care to add the reaction mix below the mineral oil.
6. Reactions were incubated at 63° C. for 5 hours in a thermal cycler.
7. The reaction plate was read using the following settings on a CytoFluor® Series 4000 Fluorescence Multi-Well Plate Reader:

| Cycle 1 | Cycle 2 |
| --- | --- |
| Excitation = 485/20 | Excitation = 560/20 |
| Emission = 530/25 | Emission = 620/40 |
| Gain = 40 | Gain = 46 |
| Reads/well = 10 | Reads/well = 10 |

8. QA acceptance criteria for positive and negative samples:

TABLE 5

Mix 1 criteria.

| Ratio | FamFOZ | RedFOZ | Genotype |
| --- | --- | --- | --- |
| >0.35 | >=1.75 | >=2.0 | Positive |
| >0.35 | <1.75 | >=2.0 | EQ |
| <0.2 | NA | >=2.0 | Negative |
| >=0.200 and <=0.35 | NA | >=2.0 | EQ |
| NA | NA | <2.0 | Low signal |

Ratio = FAMFOZ-1 (Adj to 0.01 if <=0)/RedFOZ-1

TABLE 6

Mix 2 criteria.

| Ratio | FamFOZ | RedFOZ | Genotype |
| --- | --- | --- | --- |
| >0.25 | >=1.5 | >=2.0 | Positive |
| >0.25 | <1.5 | >=2.0 | EQ |
| <0.125 | NA | >=2.0 | Negative |
| >=0.125 and <=0.25 | NA | >=2.0 | EQ |
| NA | NA | <2.0 | Low signal |

Ratio = FAMFOZ-1 (Adj to 0.01 if <=0)/RedFOZ-1

TABLE 7

Mix 3 criteria.

| Ratio | FamFOZ | RedFOZ | Genotype |
| --- | --- | --- | --- |
| >0.275 | >=1.5 | >=2.0 | Positive |
| >0.275 | <1.5 | >=2.0 | EQ |
| <0.15 | NA | >=2.0 | Negative |
| >=0.15 and <=0.275 | NA | >=2.0 | EQ |
| NA | NA | <2.0 | Low signal |

Ratio = FAMFOZ-1 (Adj to 0.01 if <=0)/RedFOZ-1

TABLE 8

Mix 4 criteria.

| Ratio | FamFOZ | RedFOZ | Genotype |
| --- | --- | --- | --- |
| >0.5 | >=1.75 | >=2.0 | Positive |
| >0.5 | <1.75 | >=2.0 | EQ |
| <0.225 | NA | >=2.0 | Negative |
| >=0.225 and <=0.5 | NA | >=2.0 | EQ |
| NA | NA | <2.0 | Low signal |

Ratio = FAMFOZ-1 (Adj to 0.01 if <=0)/RedFOZ-1

TABLE 9

Mix 5 criteria.

| Ratio | FamFOZ | RedFOZ | Genotype |
| --- | --- | --- | --- |
| >0.9 | >=1.75 | >=2.0 | Positive |
| >0.9 | <1.75 | >=2.0 | EQ |
| <0.7 | NA | >=2.0 | Negative |
| >=0.7 and <=0.9 | NA | >=2.0 | EQ |
| NA | NA | <2.0 | Low signal |

POOL 5

Ratio = FAMFOZ-1/RedFOZ-1
FAMFOZ-1 adj 0.01 if <=0
RedFOZ >=2
Ratio <0.7 is NEG
Ratio >=0.7 and <=0.9 is EQ
Ratio >0.9
FFOZ >=1.75 is POS
FFOZ <1.75 is EQ Ratio = FAMFOZ-1 (Adj to 0.01 if <=0)/RedFOZ-1

Example 3

Reagents and Methods for Detection of the ΔF508 Mutation in Cystic Fibrosis Transmembrane Conductance Regulator (CFTR) Gene in a Biplex Format Reagents:
CFTR (ΔF508) Control 1 (WT) (1 vial marked "C1", 250 µl)
CFTR (ΔF508) Control 2 (HET) (1 vial marked "C2", 250 µl)
CFTR (ΔF508) Control 3 (MT) (1 vial marked "C3", 250 µl)
Control 4 (No Target Blank) (1 vial, marked "C4", 1250 µl)
Reagent Storage:
Store at −20° C.
Reagent Composition:
CFTR (ΔF508) Control 1 (WT), CFTR (ΔF508) Control 2 (HET), and CFTR (ΔF508) Control 3 (MT) are synthetic oligonucleotides suspended in yeast tRNA and buffered nuclease-free water. Control 4 (No Target Blank) contains yeast tRNA in buffered nuclease-free water.
CONTROL USAGE:
1. Determine the number (singlicate, duplicate, triplicate, quadruplicate) of controls to be tested. Use 10 µl of control material in each reaction.
2. Treat control materials the same as test samples throughout the INVADER® DNA Assay.
3. Control materials and test samples should be analyzed on a fluorescence plate reader.

Expected Results:

CFTR (ΔF508) Control 1 material should react with only the CFTR (ΔF508) WT Primary Probe (F dye signal); CFTR (ΔF508) Control 3 material should react with only the CFTR (ΔF508) MT Primary Probe (R dye signal); CFTR (ΔF508) Control 2 material should react with both the CFTR (ΔF508) Primary Probes (F dye and R dye signals); and Control 4 (No Target Blank) material should show no specific reaction with either one or both of the CFTR (ΔF508) Primary Probes (F dye and R dye signals). Actual signal values depend on reaction volumes, test methods, and the fluorescence plate reader used.

We evaluated the effectiveness of our design by testing the assay on characterized genomic samples, where available, and synthetic oligonucleotide targets when no genomic samples could be obtained. The first set of INVADER® oligonucleotides placed the F508C polymorphism at position −1, one of the critical bases required for specificity. This set did not detect the F508C DNA. The second set, designed to detect the wild type DNA in the presence of all polymorphisms, placed the polymorphisms at positions 3, 7 and 10, respectively.

A second requirement was the proper discrimination of ΔF508 and ΔI507. The detection of the mutation ΔI507 is relegated to a separate test; the purpose of the 508 test is to report only the ΔF508 mutation. However, the ΔF508 and ΔI507 sequences are extremely similar, differing by only one base. Due to the INVADER assay's tolerance of a mismatch at specific positions, we incorporated a second, adjacent mismatch into the ΔF508 probe to avoid detection of the ΔI507 sequence. This resulted in a mismatch at position 5 on the ΔF508 target, and at positions 4 and 5 on the ΔI507 target. The mismatch at position 5 is tolerated by the assay, generating robust signal on the ΔF508 target, while the two adjacent mismatches at positions 4 and 5 are sufficient to prevent signal generation from the ΔI507 target.

We claim:

1. A kit comprising a detection assay configured for detecting the ΔF508 CFTR allele, wherein said detection assay is able to discriminate between ΔI507 and said ΔF508 CFTR allele, wherein said detection assay comprises first and second oligonucleotides configured to form an invasive cleavage structure in combination with a target sequence comprising said ΔF508 CFTR allele, wherein said first oligonucleotide comprises a 5' portion and a 3' portion, wherein said 3' portion is configured to hybridize to said target sequence, wherein said 5' portion is configured to not hybridize to said target sequence, and wherein said second oligonucleotide comprises a 5' portion and a 3' portion, wherein said 5' portion is configured to hybridize to said target sequence, and wherein said 3' portion is configured to not hybridize to said target sequence, and wherein said 3' portion of said first oligonucleotide consists of: i) the following sequence: 3'-ACCGTGGTAATTTCTTT-TATAATAAC-5', and ii) a 3' blocking group; and wherein the 5' terminal base of said sequence is attached to said 5' portion of said first oligoniucleotide.

2. The kit of claim 1, wherein said second oligonucleotide sequence comprises SEQ ID NO:81.

* * * * *